United States Patent [19]
Carruthers et al.

[11] Patent Number: 5,527,320
[45] Date of Patent: Jun. 18, 1996

[54] SURGICAL CLIP APPLYING INSTRUMENT

[75] Inventors: Harold G. Carruthers, Durham; Stephen J. Dawes; Angela S. Phillips, both of Raleigh; David L. Foshee, Apex, all of N.C.

[73] Assignee: Pilling Weck Inc., Research Triangle Park, N.C.

[21] Appl. No.: 194,479

[22] Filed: Feb. 10, 1994

[51] Int. Cl.$^6$ ................................................ A61B 17/00
[52] U.S. Cl. .................... 606/143; 606/139; 606/142; 227/901
[58] Field of Search ..................... 606/142, 143, 606/139, 205, 208; 227/901, 19, 175

[56]        References Cited

U.S. PATENT DOCUMENTS

| | | |
|---|---|---|
| Re. 28,932 | 8/1976 | Noiles et al. . |
| D. 305,064 | 12/1989 | Mulhauser et al. . |
| 2,296,493 | 9/1942 | Bernstein . |
| 3,404,457 | 10/1968 | Swanstrom . |
| 3,675,688 | 7/1972 | Bryan et al. . |
| 4,086,926 | 5/1978 | Green et al. ............... 606/143 |
| 4,196,836 | 4/1980 | Becht . |
| 4,246,903 | 1/1981 | Larkin . |
| 4,296,751 | 10/1981 | Blake, III et al. . |
| 4,372,295 | 2/1983 | Heckele . |
| 4,496,090 | 1/1985 | Crevier et al. . |
| 4,509,518 | 4/1985 | McGarry et al. . |
| 4,532,925 | 8/1985 | Blake, III . |
| 4,550,715 | 11/1985 | Santangelo et al. . |
| 4,562,839 | 1/1986 | Blake, III et al. . |
| 4,598,711 | 7/1986 | Deniega . |
| 4,616,650 | 10/1986 | Green et al. . |
| 4,656,999 | 4/1987 | Storz . |
| 4,662,373 | 5/1987 | Montgomery et al. . |
| 4,691,853 | 9/1987 | Storace . |
| 4,712,549 | 12/1987 | Peters et al. . |
| 4,759,364 | 7/1988 | Boebel . |
| 4,850,355 | 7/1989 | Brooks et al. . |
| 5,000,745 | 3/1991 | Guest et al. . |
| 5,009,391 | 4/1991 | Steigerwald . |
| 5,030,226 | 7/1991 | Green et al. . |
| 5,047,038 | 9/1991 | Peters et al. . |
| 5,049,152 | 9/1991 | Simon et al. . |
| 5,059,201 | 10/1991 | Asnis . |
| 5,084,057 | 1/1992 | Green et al. . |
| 5,100,420 | 3/1992 | Green et al. . |
| 5,104,394 | 4/1992 | Knoepfler . |
| 5,104,395 | 4/1992 | Thorton et al. . |
| 5,112,343 | 5/1992 | Thornton . |
| 5,156,608 | 10/1992 | Troidl et al. . |
| 5,163,945 | 11/1992 | Ortiz et al. . |
| 5,171,247 | 12/1992 | Hughett et al. . |
| 5,171,250 | 12/1992 | Yoon . |
| 5,395,381 | 3/1995 | Green et al. ............... 606/143 |

*Primary Examiner*—Stephen C. Pellegrino
*Assistant Examiner*—Jeffrey A. Schmidt
*Attorney, Agent, or Firm*—Rosenblatt & Redano

[57]          ABSTRACT

The surgical instrument system disclosed is particularly useful for endoscopic procedures. In the preferred embodiment, a hemostatic clip applicator can be directly connected to a trigger assembly or indirectly connected to the trigger assembly through the use of an extension. The connection between the extension and the clip applicator is secured to prevent accidental release during the procedure. The applicator receives a longitudinal input and translates the input into relative component motion through the use of gearing to apply the clips. The handle stem assembly in an alternative embodiment has a drive rod configuration that connects to a closure member so as not only to provide the distal biasing force, but also to provide, if needed, a proximal pulling force to assist in release of the jaw if it becomes necessary.

29 Claims, 21 Drawing Sheets

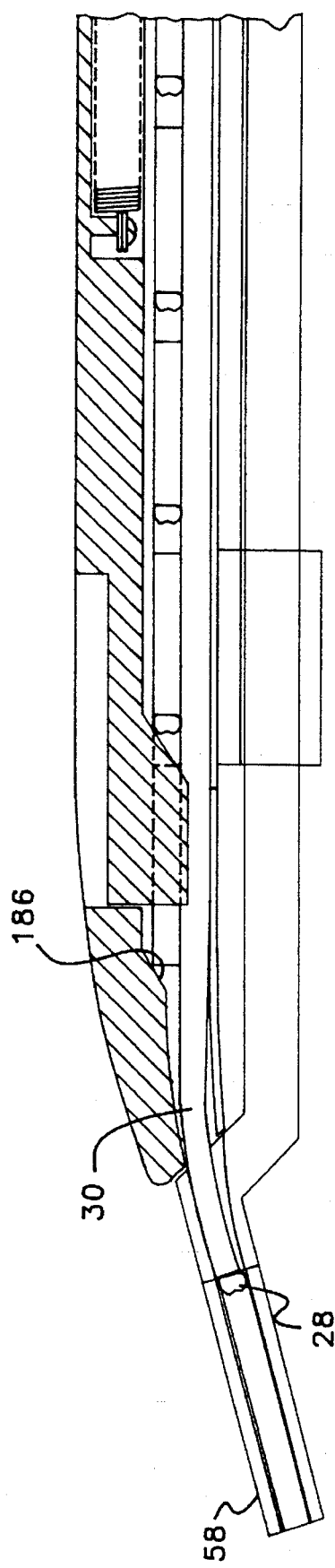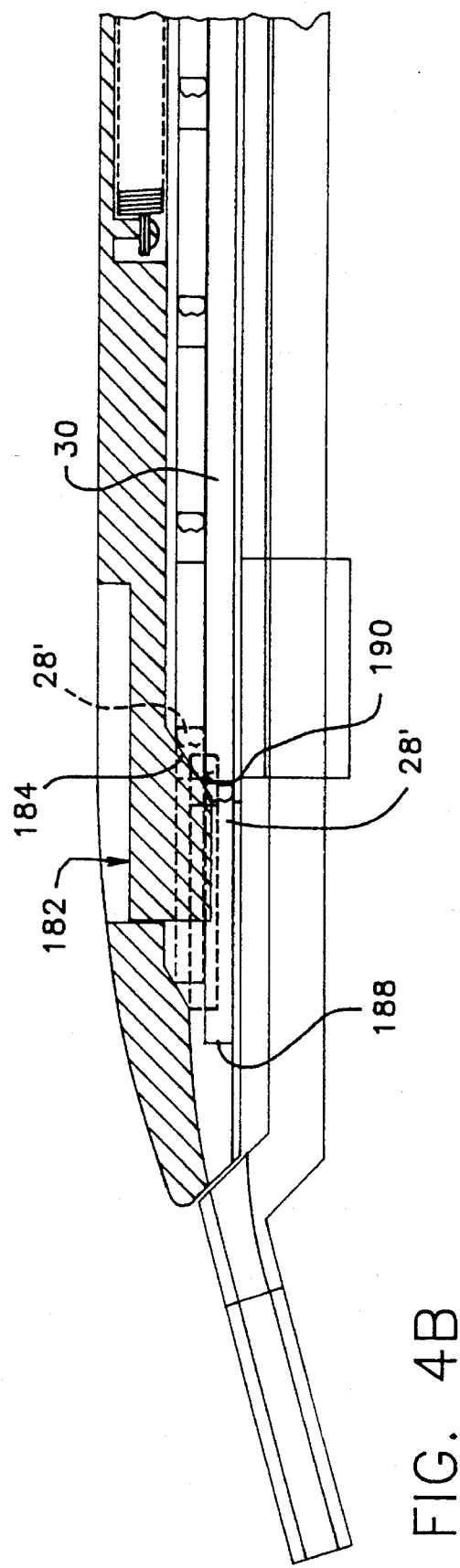
FIG. 4A
FIG. 4B

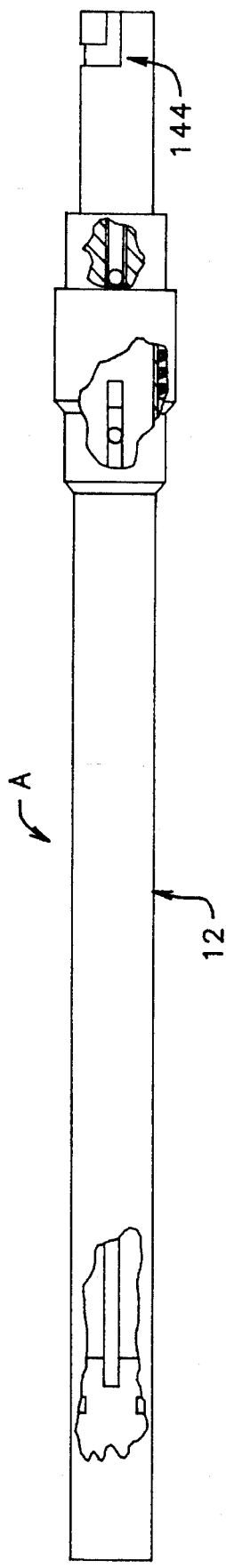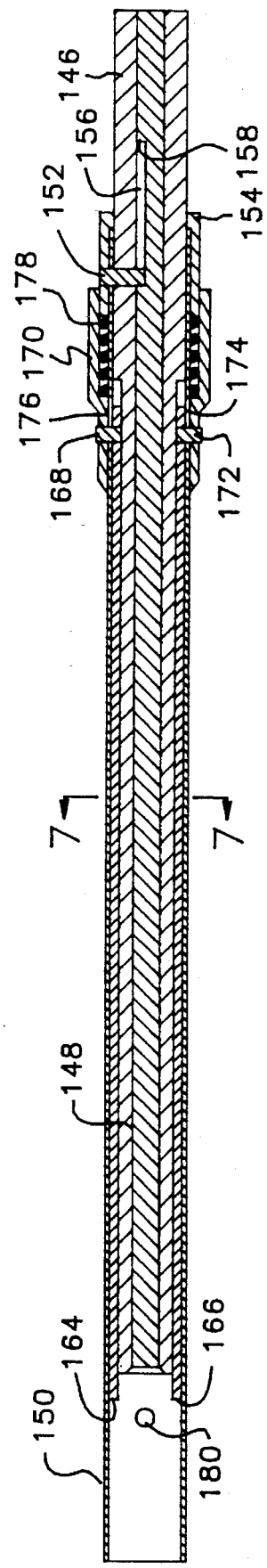
FIG. 5
FIG. 6

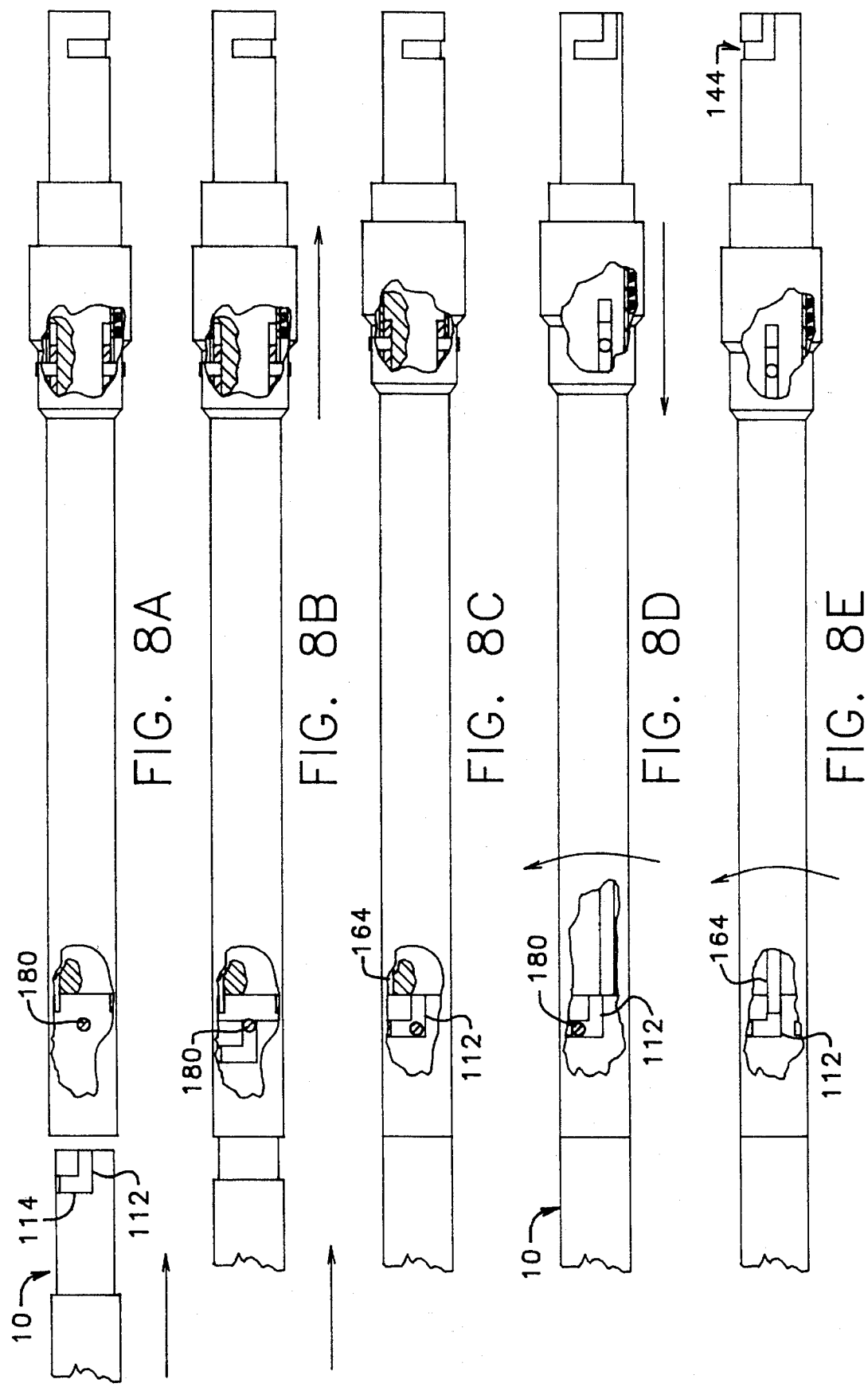

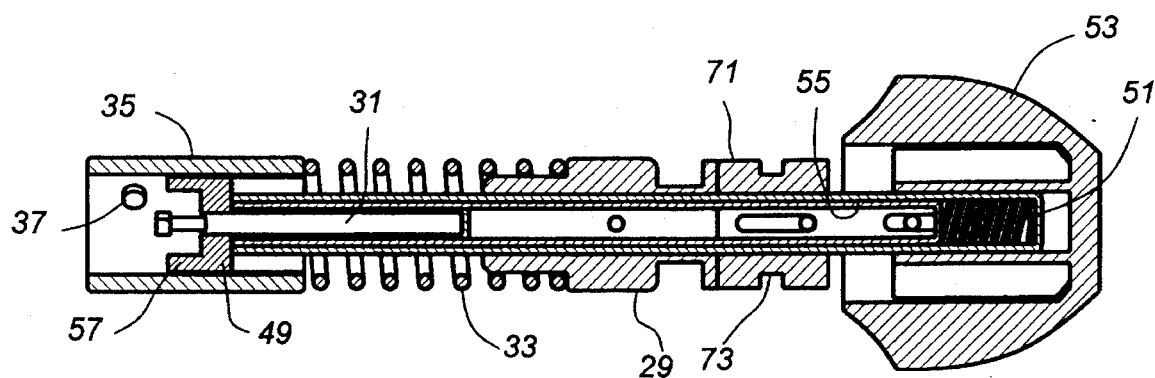
FIG. 14
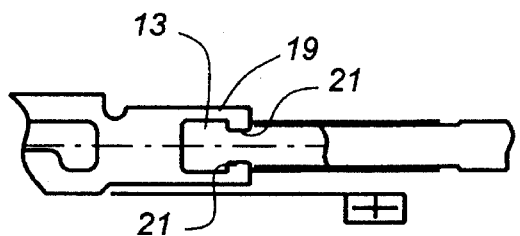
FIG. 15
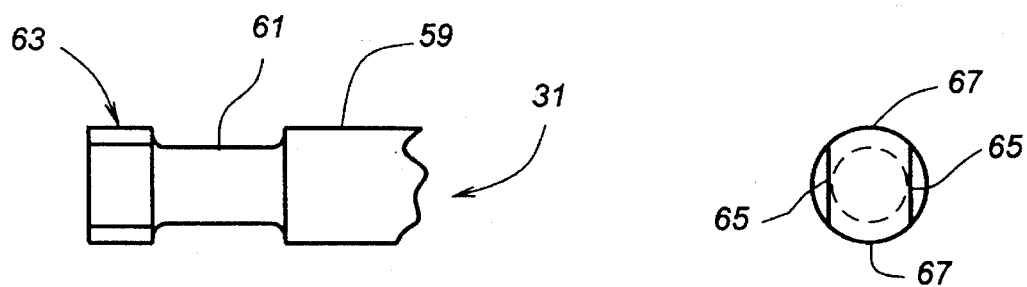
FIG. 16A       FIG. 16B

5,527,320

SURGICAL CLIP APPLYING INSTRUMENT

FIELD OF THE INVENTION

The field of the invention relates to surgical instruments, more particularly those that can be used in endoscopic surgery with the emphasis on applying hemostatic clips.

BACKGROUND OF THE INVENTION

Endoscopic surgery frequently requires the application of hemostatic clips or the use of other instruments which can ligate, grab or rip for a variety of purposes. Several significant characteristics of such instruments need to be simplicity in construction, reliability in operation, as well as low cost. Components that come into contact with internal organs in the body must also be effectively sterilized. Alternatively, the construction needs to be sufficiently economical to allow disposability of contaminated components. The layout of the instrument needs to be such as to give the surgeon good feedback during the procedure as to allow as much control as possible while using the instrument. If component systems are used, it is important to have them securely attached to each other to avoid disconnection during the procedure which could jeopardize the patient's condition should detachment occur during a procedure.

Surgical instruments that are adaptable to more than one procedure are preferred. A versatile system of surgical instruments which allows different types of instruments to be used in conjunction with a given actuating system is also a desirable feature.

In the past, various surgical instruments have been developed which address some, but not all of these needs. Some of the problems in addressing many of these needs is that a solution to one of such needs works at cross purposes to another. The result in the past has been fairly complex instruments which have adequately addressed one or two of such design requirements while compromising on the others. Hemostatic clip applicators of varying complexity are known in the art as exemplified by U.S. Pat. Nos. 5,049,152; 5,084,057; 5,100,420; 5,163,945; 4,496,090; 3,675,688; and Reissue 28,932. Some of these patents reveal the use of a trigger grip to actuate a rod which motion is transferred directly to an operating component for accomplishing the purpose the instrument. Typical of such devices is U.S. Pat. No. 4,759,364 which illustrates pincers that are rod actuated. Yet, other clip appliers use a scissor grip and linkage in combination with spring forces to accomplish the clip application. U.S. Pat. No. 5,104,395 illustrates this principle. Other clip applicators that work in a similar fashion employ a ratcheted counterwheel, wherein, every time a clip is applied, the wheel is rotated giving a visual display to the surgeon of the number of clips remaining. This type of clip applier is shown in U.S. Pat. No. 5,047,038. Alternatively, to a ratcheted wheel indicating the number of clips remaining, transparent covers, such as shown in U.S. Pat. No. 5,104,395 have also been used to allow the surgeon to see how many clips remain in the stack.

Outside the medical field, staplers have been used to hold objects together, such as in upholstery construction. Typical of such staplers is U.S. Pat. No. 2,296,493 illustrating a hand-operated stapling machine using a rack and pinion linkage with regard to the staple feeding operation.

The apparatus of the present invention has the objectives of providing a simple and economical construction that gives good feedback in the surgeon's hand as to the procedure being conducted. A system of components is provided which has reusable and disposable features. The connection system between the components gives certainty of fixation, thereby eliminating the risk of accidental disconnection during a procedure within the body. The system also provides for adjustability for using clips of various lengths or widths. The clip applicator also provides a feature to ensure sufficient jaw opening prior to feeding of the next successive clip. This avoids the hazards of jamming.

SUMMARY OF THE INVENTION

The surgical instrument system disclosed is particularly useful for endoscopic procedures. In the preferred embodiment, a hemostatic clip applicator can be directly connected to a trigger assembly or indirectly connected to the trigger assembly through the use of an extension. The connection between the extension and the clip applicator is secured to prevent accidental release during the procedure. The applicator receives a longitudinal input and translates the input into relative component motion through the use of gearing to apply the clips. The handle stem assembly in an alternative embodiment has a drive rod configuration that connects to a closure member so as not only to provide the distal biasing force, but also to provide, if needed, a proximal pulling force to assist in release of the jaw if it becomes necessary.

BRIEF DESCRIPTION OF THE DRAWINGS

FIGS. 4A–4F are sectional elevational views of the applicator with the feeder in various positions.

FIG. 5 illustrates the extension member with a partial cutaway showing its operation.

FIG. 6 is a section view of the extension member of FIG. 5.

FIG. 8A shows the alignment of the applicator to the extension;

FIG. 8B shows insertion of the extension into the applicator;

FIG. 8C shows further extension of the extension over the applicator;

FIG. 8D illustrative relative rotation as between the applicator and the extension; and FIG. 8E shows the secured position between the applicator and the extension.

FIG. 14 is a sectional elevational view of the handle stem assembly.

FIG. 15 is a plan view of the proximal end of the closure member.

FIG. 16A is at sectional elevational view of the distal end of the drive rod; and FIG. 16B is an end view of the view shown in FIG. 16A.

DETAILED DESCRIPTION OF THE PREFERRED EMBODIMENT

The apparatus A of the present invention is an instrument, or a variety of instruments, useful for endoscopic or less invasive surgeries. The major components in the preferred embodiment are a clip applicator generally referred to as 10 (see FIG. 1); an extension member 12 (see FIG. 5); and an actuator 14 (see FIG. 9). These components can be used altogether or, alternatively, the actuator 14 can be applied directly to the clip applicator 10. Alternatively, actuator 14 can be used with other types of surgical instruments which are operable by longitudinal input movement which creates a relative movement in response to an input force to accomplish a surgical procedure.

Figure 1:
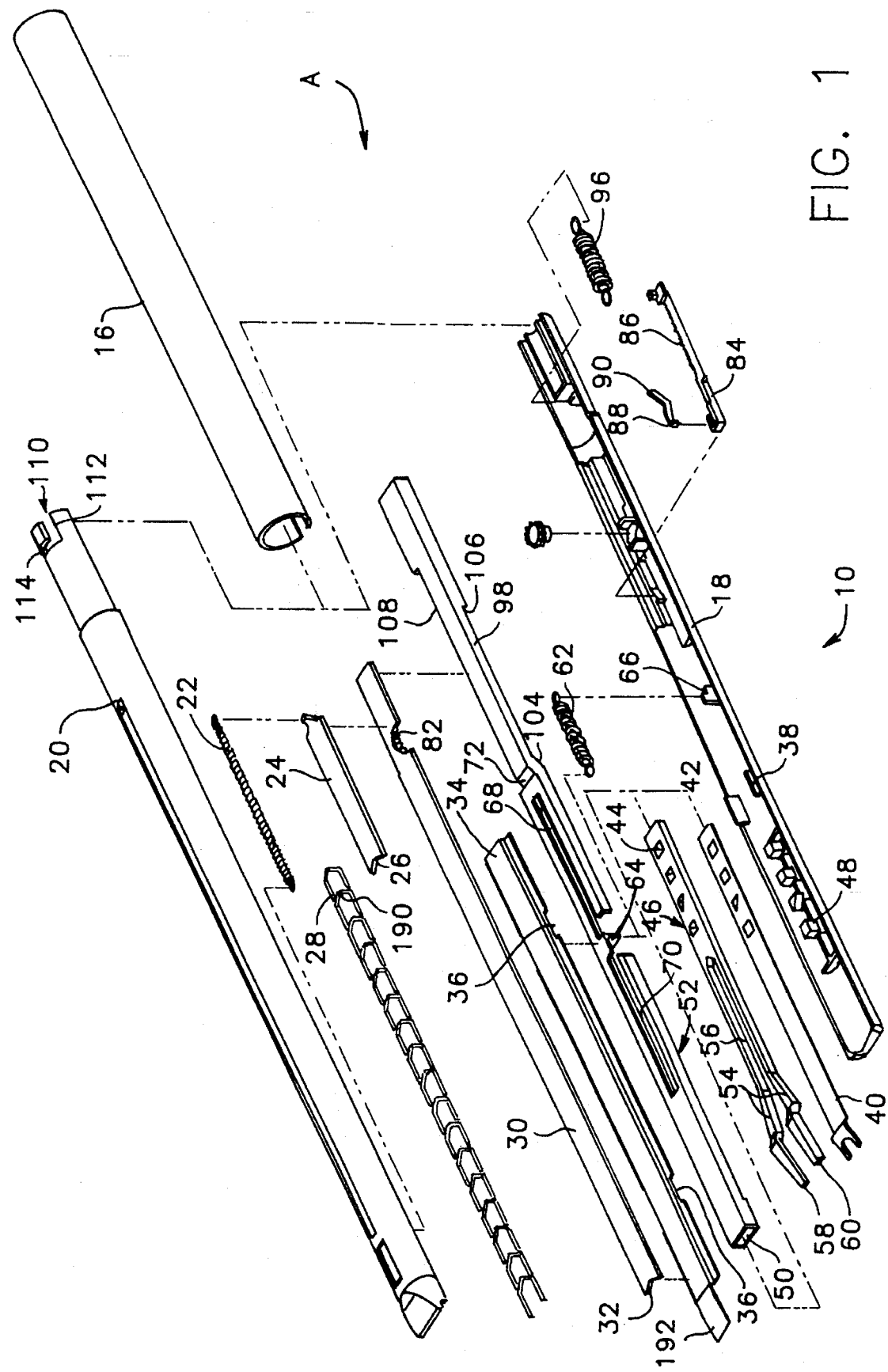
FIG. 1 depicts an exploded view showing the assembly of the components of the clip applicator.

Referring now to FIG. 1, the details of the construction and operation of the clip applicator 10 will be described. A cover tube 16 holds bottom housing 18 and top cartridge 20 together. A pusher spring 22 is connected at its distal end to top cartridge 20 and at its proximal end to pusher 24. The proximal end of pusher 24 has a pushing surface 26 which is a surface conforming to the clip 28. In the preferred embodiment, a series of clips 28 can be stacked end-to-end in front of pushing surface 26; however, the scope of the invention is broad enough to include an applicator that applies one or more clips in sequence. The clips 28 rest on a feeder 30 as does pusher 24. The distal end of feeder 30 comprising a pushing surface 32 which, like pushing surface 26, conforms to the body shape of the clips 28 for the purpose of further advancing a clip as will be described below. The feeder 30 rests on cartridge floor 34. It should be noted that the assembly of the top cartridge 20, pusher spring 22, pusher 24, clips 28, feeder 30 and cartridge floor 34 can be assembled as subassembly. The cartridge floor 34 has a plurality of cutouts 36 on both sides of its longitudinal centerline. A plurality of posts 38 conform to the shape of cutouts 36 and align the top cartridge 20 and the cartridge floor 34 to bottom housing 18.

Vessel stop 40 has a plurality of cutouts 42 which are aligned with cutouts 44 on jaw 46. Vessel stop 40 prevents vessel from dislodging clip 28. Jaw 46 and vessel stop 40 are put together by aligning openings 42 and 44 onto posts 48 in bottom housing 18 after initially slipping the assembly of vessel stop 40 and jaw 46 through the distal end 50 of closure member 52. Jaw 46 has a pair of opposed tapered surfaces 54 at the distal end of an elongated slot 56. Mounted distally to the tapered surfaces 54 are crimping members 58 and 60. Closure member 52 is mounted within housings 18 and 20 and can translate responsive to a force input. A spring 62 connected at its distal end to tab 64 on closure member 52 and on its proximal end to post 66 on bottom housing 18 applies a force in the proximal direction to closure member 52. Slot 68 on closure member 52 accommodates spring 62. Posts 48 in bottom housing 18 extend through openings 42 and 44 and into slot 70 on closure member 52, thereby, in the preferred embodiment, limiting the amount of travel of closure member 52 in the distal direction. While a transition 72 is illustrated to accommodate the placement of the floor 34 over the closure member 52, the apparatus A of the present invention encompasses a closure member that does not necessarily include such a transition surface 72.

Figure 2A:
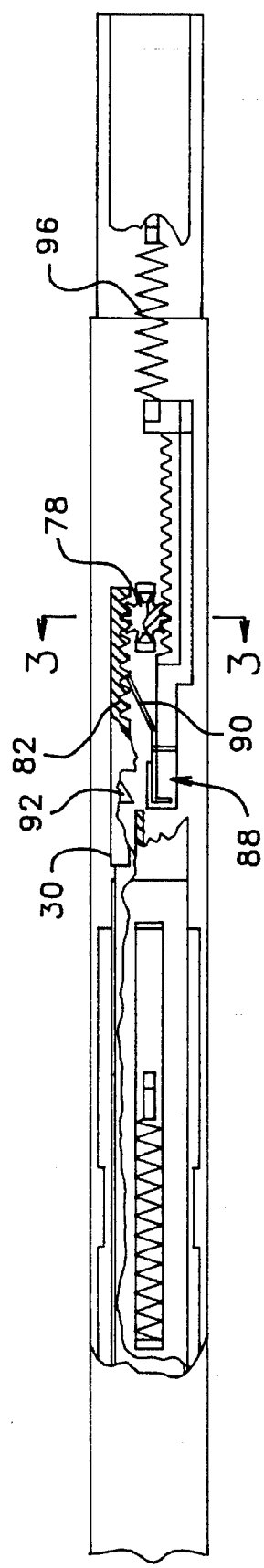
FIGS. 2A–2C are partial cutaway top views of the applicator as shown in FIG. 1 in a fully assembled condition and further illustrating the idler feature of the feeder.
Figure 2B:
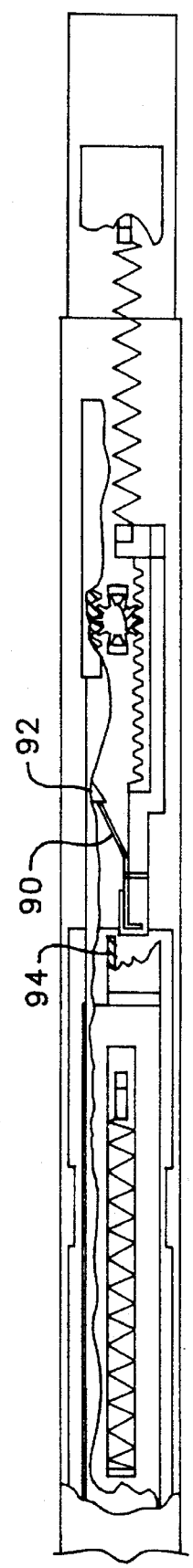
Figure 2C:
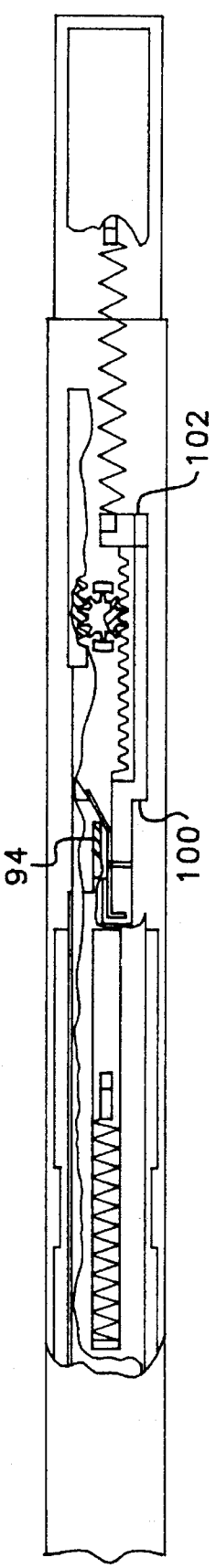
Figure 3:
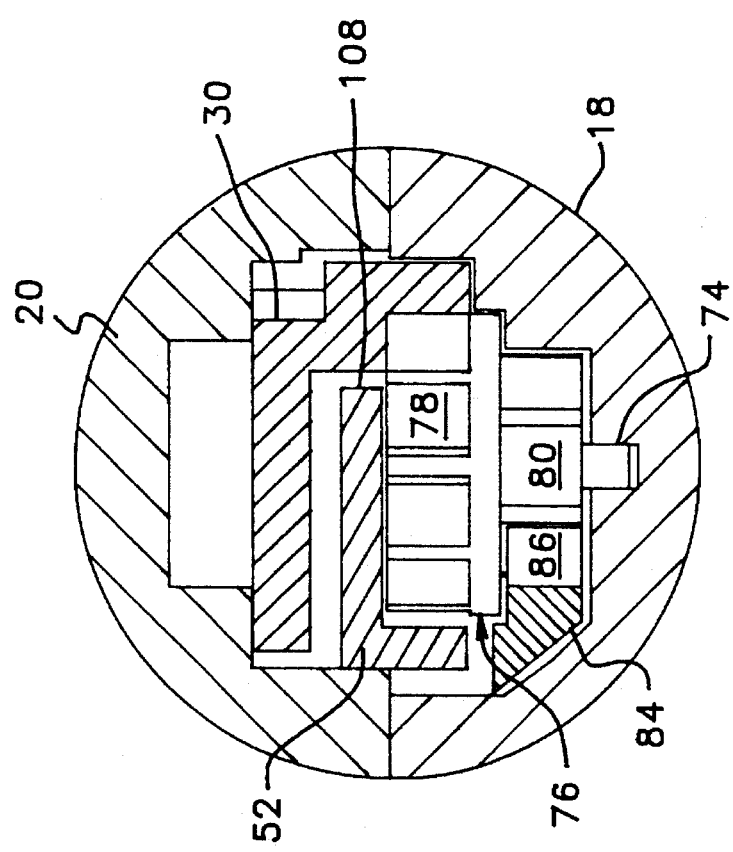
FIG. 3 is the view at section lines 3—3 shown in FIGS. 2A–2C.

Referring now to FIGS. 2A–2C and 3, bottom housing 18 accommodates spindle 74 of gear 76. Gear 76 is a compound gear, which, in the preferred embodiment, is really two gears parallel to each other supported by spindle 74. In the preferred embodiment, gear 76 has an upper gear 78 and a lower gear 80. The diameters and hence the number of teeth in gears 78 and 80 are different. The dictates of design determine the ratio of teeth and diameters of the gears 78 and 80 based on the degree of relative movement desired for the application. Different sized clips can be accommodated in the same applicator 10 by varying this ratio. While gears are recited, other motion reversing mechanisms are within the purview of the invention. This includes pulley systems as well as wheels that rely on friction to reverse motion, as well as lever assemblies. Spindle 74 may be motorized or powered to accomplish reverse motion as opposed to an input force to closure member 52 or to feeder 30 which are preferably stacked. Referring to FIGS. 1 and 2A–2C, it can be seen that feeder 30 has a plurality of teeth 82 which are visible in FIG. 1 due to a partial cutaway. Another view of teeth 82 is illustrated in FIGS. 2A–2C. As indicated in FIGS. 2A–2C and 3, teeth 82 engage substantially in the same plane with upper gear 78. Lower gear 80 is substantially in the same plane as idler rack 84. Idler rack 84 has a plurality of teeth 86 which engage lower gear 80. As seen in FIGS. 1 and 3, teeth 82 face teeth 86 on opposite sides of longitudinal axis of cover tube 16 with teeth 82 being in a higher plane than teeth 86 of idler rack 84. Mounted to the distal end of idler rack 84 is rack latch 88. Rack latch 88 has a cantilevered and inclined finger 90. As shown in FIGS. 2A–2C, finger 90 extends obliquely toward teeth 82 but is in a plane below such teeth such that upon distal movement of closure member 52, finger 90 skips over tab 92 as shown by comparing the top two views of FIG. 2A–2C. When the closure member 52 moves in the proximal direction, a tab 94, which extends downwardly from the closure member parallel to its longitudinal axis, engages finger 90 and moves it up and over tab 92. The proximal end of idler rack 84 is connected to spring 96 with the proximal end of spring 96 secured to the bottom housing 18, as shown in FIG. 1. The underside of closure member 52 has a notched area 98, as shown in FIG. 1. Idler rack 84 has a shoulder 100 and an opposed shoulder 102. The notched area 98 in closure member 52 is defined by shoulders 104 and 106 (see FIG. 1). The distance between shoulders 100 and 102 is smaller than the distance between shoulders 104 and 106 for a purpose which will be described below. Closure member 52 has a notched surface 108 to accommodate the feeder 30, as shown in the section view of FIG. 3.

Figure 9:
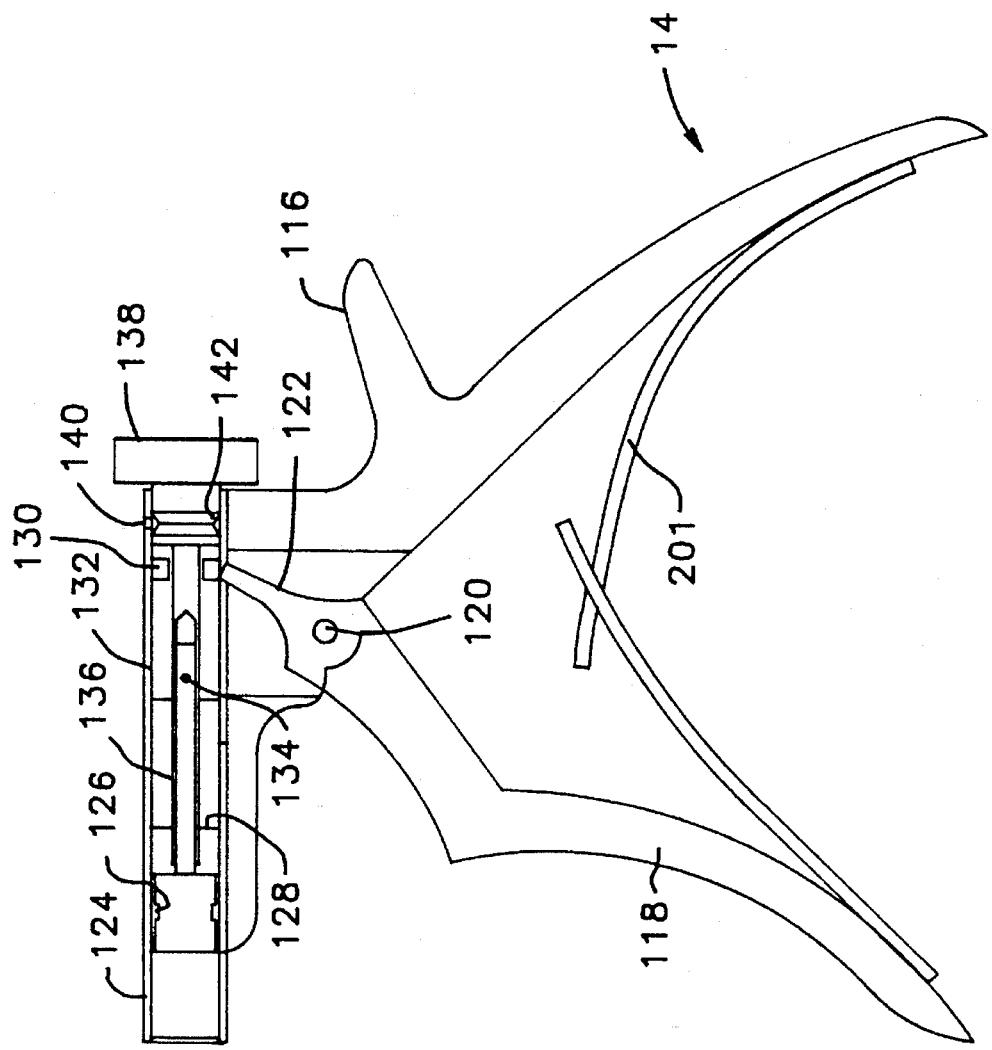
FIG. 9 is the operating mechanism in an open position.
Figure 10:
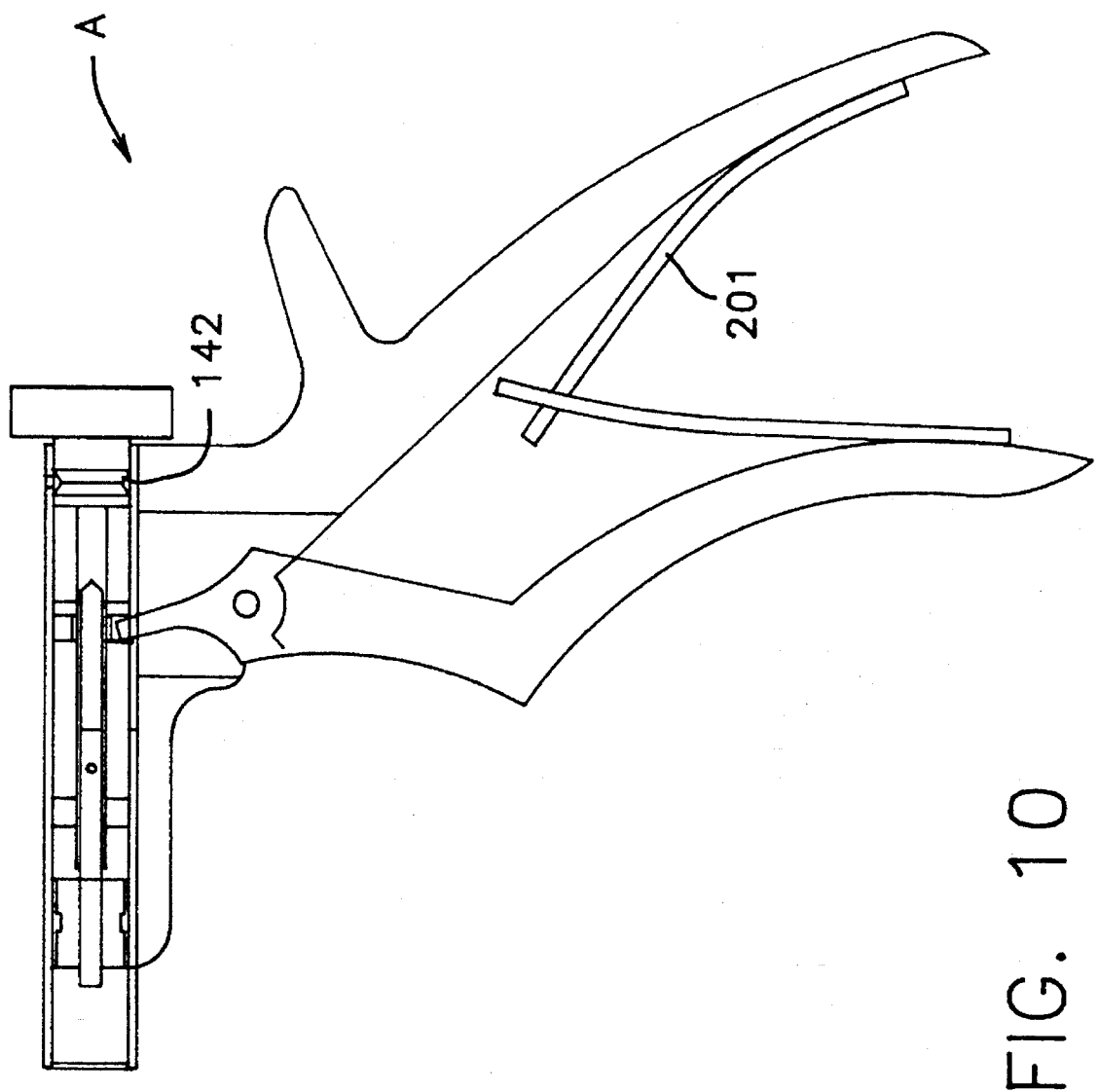
FIG. 10 is the operating mechanism in a closed position.

The operation of the clip applicator 10 is initiated by a force supplied to closure member 52. Prior to getting into the details of the operation of clip applicator 10, the operation of the extension member 12 and actuator 14 will be described. FIG. 1 illustrates that the top cartridge 20 has an L-shaped slot 110, which has a longitudinal component 112 and a radial component 114. While only one L-shaped slot is shown in FIG. 1, those skilled in the art can appreciate that a plurality of such L-shaped slots 110 can be employed for the purposes of securing the clip applicator 10 either to the extension member 12 or the actuator 14. The actuator 14 in its two positions is illustrated in FIGS. 9 and 10. A handle 116 is mounted to a trigger 118 at pin 120. Trigger 118 has an extension tab 122 which extends into barrel 124o At least one pin 126 extends into barrel 124 and holder 128. Pin or pins 126 are mounted into a position so as to engage L-shaped slot 110 (see FIG. 1) of top cartridge 20. Through a bayonet-type mounting, the clip applicator 10 is longitudinally inserted so that longitudinal component 112 of L-shaped slot 110 passes by pin or pins 126. The clip applicator 10 is then rotated to move the radial component 114 of L-shaped slot 110 past pin or pins 126 to secure the attachment. It should be noted that there is a pin 126 for each L-shaped slot 110 provided in top cartridge 120.

Tab 122 extends into barrel 124 and engages a groove 130 on sleeve 132. A dowel 134 fixes rod 136 to sleeve 132. A knob 138 is rotatably mounted on its central axis to barrel 124 and is retained against longitudinal movements by virtue of pin 140 extending into groove 142 of sleeve 132. When the clip applicator 10 is inserted into barrel 124 and engaged on pins 126, rod 136 is aligned with closure member 52. As a result, moving the trigger from the position shown in FIG. 9 to the position shown in FIG. 10, translates sleeve 132 and rod 136 distally, which, in turn, begins distal movement of closure member 52. It should be noted that the connection, as illustrated in FIGS. 9 and 10, is not a fail-safe connection in the sense that rotation of the clip applicator 10 can result in disengagement from actuator 14. However, without the use of extension member 12, the procedure being done with the clip applicator 10 connected directly to the actuator 14 is primarily not very deep within the body of the patient; therefore, making the security of the attachment a lesser concern than in a situation involving an endoscopic procedure. However, the connection, as previously described, at the distal end of barrel 124 involving pins 126 can be fashioned differently along the lines as will be described with reference to FIGS. 5–7 so as to provide a fail-safe connection if the clip applicator 10 is connected directly to the actuator 14.

It should be noted that the trigger 118 returns from its closed position shown in FIG. 10 to its open position shown in FIG. 9 by virtue of spring 201.

Figure 7:
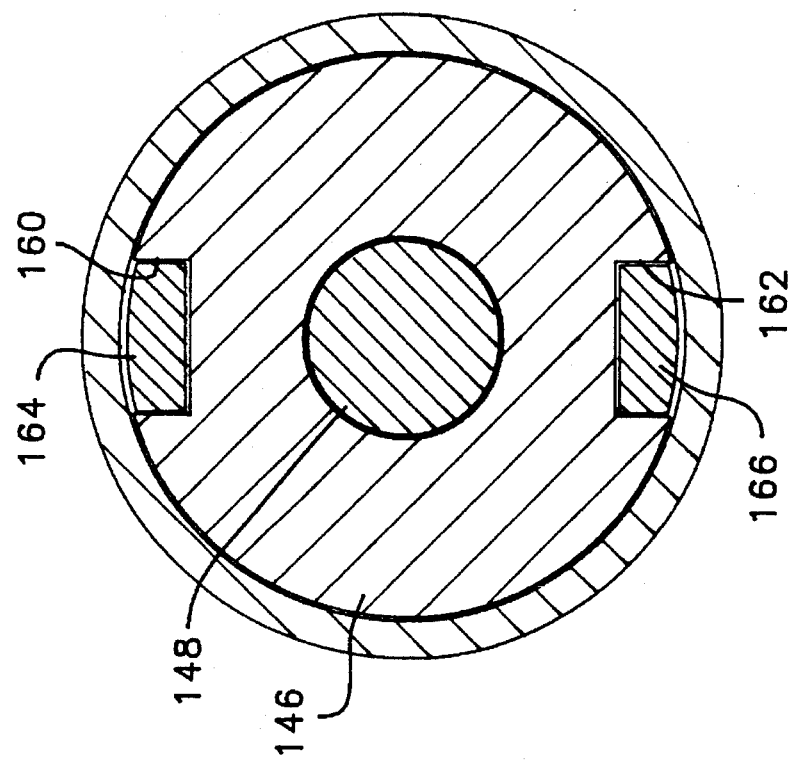
FIG. 7 is the view along section 7—7 shown in FIG. 6.

At times it may be desirable to use the apparatus A of the present invention in an endoscopic procedure. When doing so, the extension member 12 becomes an additional advantage. Referring to FIG. 5, the outer assembly of the extension member 12 is illustrated. An L-shaped slot 144 is at the proximal end of extension member 12 and is for the same purpose as previously described in L-shaped slot 110. L-shaped slot 144 is disposed in guide 146 which extends the substantial length of extension member 12. Concentrically mounted to guide 146 is extension rod 148. Also, concentrically mounted with respect to guide 146 is tube 150. Tube 150 is secured to guide 146 by pin 152 which extends radially through guide 146, tube 150, and fixed cuff 154. Extension rod 148 has a longitudinal slot 156 to allow extension rod 148 to translate with respect to pin 152 with pin 152 being a distal travel stop as shoulder 158 engages pin 152. The position of extension rod 148 corresponds to the open position of actuator 14, as shown in FIG. 9. When the actuator 14 is assembled to the extension member 12, rod 136 and extension rod 148 are in alignment for tandem movement. As shown in FIG. 7, guide 146 has a pair of opposed slots 160 and 162. Slides 164 and 166 are disposed in slots 160 and 162, respectively. A pin 168 extends through slide cuff 170 and into slide 164. Similarly, a pin 172 extends through slide cuff 170 and into slide 166. It should be noted that the tube 150 has slots 174 and 176 to allow the assembly of slide cuff 170 and slides 164 and 166 to move with respect to guide 146. A spring 178 biases slide cuff 170 distally as a result of it bearing on fixed cuff 154. One pin 180 for each L-shaped slot 110 mounted to clip applicator 10 is disposed at the distal end of extension member 12.

The L-shaped slots 110 on the clip applicator 10 are preferably identical to the L-shaped slots on the extension 12 for interchangeability with actuator 14. Likewise, the pins 180 on extension 12 are preferably identical to pins 126 on the actuator 14.

All of the components of extension member 12 having been described, the method of securing the clip applicator 10 will now be described. As shown in FIGS. 8A–8E, the longitudinal component 112 of L-shaped slot 110 is aligned with pin 180. The clip applicator 10 is advanced proximally until longitudinal slot 112 registers with pin 180, as shown as the second step in the sequence of motions in FIGS. 8A–8E. The next step requires further advancement of clip applicator 10 in the proximal direction until pin 180 bottoms in longitudinal slot 112. As the third step occurs, the slides 164 and 166 are pushed proximally from their position in the second step, which, in turn, translates slide cuff 170 and compresses spring 178. In the fourth step, the applicator 10 is rotated so that radial component 114 of L-shaped slot 110 moves past pin 180. As the rotation progresses, ultimately the longitudinal component 112 becomes aligned with a corresponding slide 164 or 166. At that time, the force of spring 178 acts on slide cuff 170, which, through pins 168 and 172, forces slides 164 and 166 distally until they are registered in longitudinal component 112. The force of spring 178 then retains the connection between extension member 12 and applicator 10 such that rotation is prevented and there is no accidental disconnection. If disconnection is desired, a force in the proximal direction must be applied to slide cuff 170 to overcome the force of spring 178 and translate slides 164 and 166 proximally to take them out of register with longitudinal component 112 of L-shaped slot 110. At that time, rotation in the opposite direction of the previous rotation reverses the steps shown in FIGS. 8A–8E and allows for disconnection between the extension member 12 and the clip applicator 10. The extension member 12 can be made of any desirable materials and, as previously stated, may have a similar connection at its proximal end, as illustrated for its distal end. This type of fail-safe connection could be positioned on the proximal end of extension member 12 in lieu of L-shaped slot 144. Accordingly, depending on the need, a fail-safe connection can be provided in the connection between the actuator 14 and the extension member 12, as well as between the extension member 12 and the clip applicator 10 and between the actuator 14 and the clip applicator 10.

Those skilled in the art will appreciate that the actuator 14 is reusable as can be extension member 12.

It should be noted that during the procedure, the surgeon can reorient the position of crimping members 58 and 60 (see FIG. 1) by applying a rotational force to knob 138 (see FIG. 9). A rotational force applied to knob 138 is transmitted through sleeve 132, dowel 134, into holder 128 and pins 126, which causes the clip applicator 10, or the combination of clip applicator 10 and extension member 12, to rotate in response to rotation of knob 138.

Referring now to FIGS. 1–4, the operation of the clip applicator 10 will now be described in detail. The process of positioning and feeding the clips 28 will be described by reference to FIGS. 4A–4F. In FIGS. 4A–4F, the feeder 30 is distally extended so that a clip 28 is between crimping members 58 and 60. Since the views of FIGS. 4A–4F are in sections, only crimping member 58 is illustrated. In the second step illustrated in FIG. 4B, the feeder 30 has been retracted thus allowing the pusher 24 (see FIG. 1) to push the clip stack 28 forward moving the next clip in line 28' through the intermediate position and final position illustrated in FIG. 4B. The pusher 24 pushes clip 28' into the delta point 182. The delta point 182 has a ramp surface 184. The top cartridge 20 has a ramp surface 186. The front end or legs 188 of clip 28' engage ramp surface 186. The first contact is made between legs 188 and ramp surface 186. After this first contact is made, the next clip in line 28' is rotated slightly before the inner apex 190 (see FIG. 1) of clip 28' contacts sloped surface 184. The next step as illustrated in FIG. 4C where the clip 28' is now in position to be fed between crimping members 58 and 60. The next step as shown in FIG. 4D where the feeder 30 is pushing the clip 28' distally. The next step is illustrated in FIG. 4E where clip 28' enters between crimping members 58 and 60.

Figure 4C:
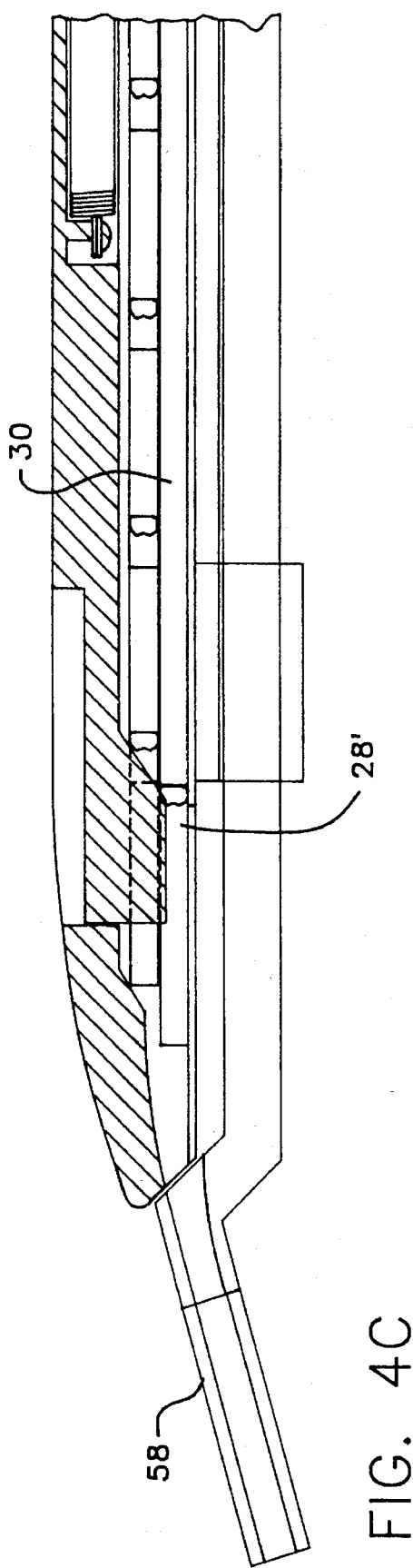
Figure 4D:
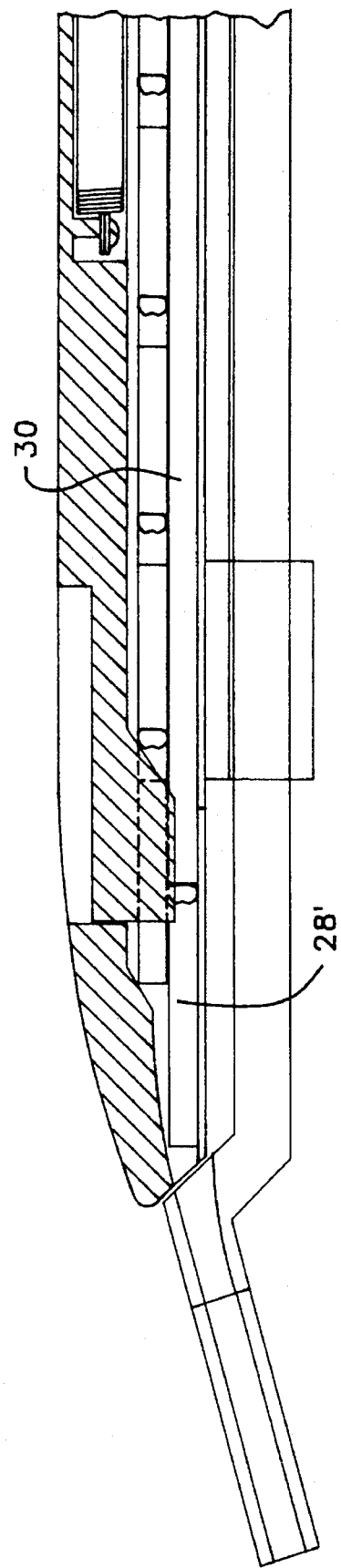
Figure 4E:
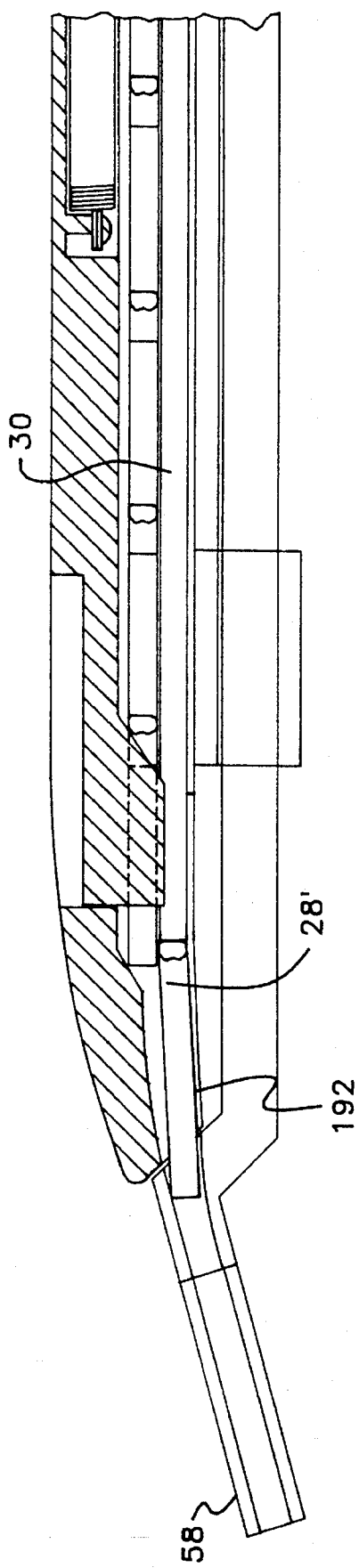
Figure 4F:
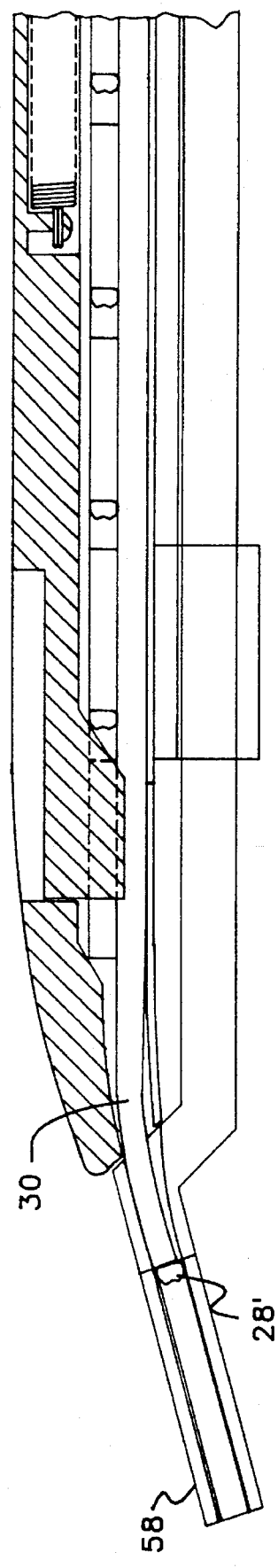

Referring now to FIG. 1, it will be seen that the cartridge floor 34 has a flexible distal segment 192. The flexibility of the cartridge floor 34 gives the clip 28' the ability to rotate into approximately a 15° angle. FIG. 4F indicates the position shown in FIG. 4A with clip 28' now ready for application.

To obtain the motions previously described with reference to FIG. 4, FIGS. 1, 2A–2C, and 9 must be reviewed. The same sequence occurs if extension 12 is mounted to actuator 14. Moving the trigger 118 from the open position of FIG. 9 into the closed position of FIG. 10 advances rod 136 which, in turn, advances rod 148, which provides a distal pushing force on closure member 52 (or first member). Closure member 52 begins to move distally. As a result of such distal movement, shoulder 106 (see FIGS. 2A–2C) of closure member 52 engages shoulder 102 on rack 84 (see FIG. 1). Thereafter, closure member 52 and idler rack 84 move in tandem. As the idler rack 84 advances, it rotates lower gear 80 (a part of the rotating assembly) as a result of the engagement of gear 80 with teeth 86 on idler rack 84. Gear 76 then rotates through the connection between upper gear 78 and teeth 82 on feeder 30 (or second member), causing feeder 30 to move in the proximal direction, as seen by comparing FIGS. 4A to 4B. Simultaneously, while the feeder is being retracted, the closure member 52 is advancing toward tapered surfaces 54. The clip 28, which was between jaws 58 and 60 is crimped as jaws 58 and 60 move toward each other when distal end 50 of closure member 52 advances against ramp surfaces 54 pushing them together. It should be noted that the feeder 30 has retracted sufficiently out of position between crimping members 58 and 60 before members 58 and 60 start moving toward each other. The sequence of these movements can be facilitated by selective placement and angularity of ramp surfaces 54 on jaw 46.

As has been explained, the operation of actuator 14 results in crimping of clip 28 as closure member 52 advances distally over jaw 46. As this is occurring, the idler rack 84 moves distally as well, allowing finger 90 to snap over tab 92, as shown in FIGS. 2A–2B, by comparing the first and second positions. With the closure member 52 fully advanced distally, the trigger 118 can be released. Spring 62 urges closure member 52 proximally allowing the crimping members 58 and 60 to spread apart. Idler rack 84 moves proximally with closure member 52 in the proximal direction until finger 90 abuts tab 92. At that point, closure member 52 can continue to move proximally due to notched area 98 being longer than the distance between shoulders 100 and 102 of idler rack 84. However, once the finger 90 hits tab 92, idler rack 84 is immobilized preventing any further distal movement of the feeder 30. The closure member 52 continues to move proximally until tab 94 engages finger 90, as shown in FIG. 2C. The continuing proximal movement of closure member 52 forces finger 90 around tab 92. When this occurs, spring 96 vigorously pulls idler rack 84 proximally until shoulder 102 contacts shoulder 106 on the closure member 52 (see FIG. 1). The sudden proximal movement of idler rack 84 turns gear 76 vigorously resulting in rapid distal movement of feeder 30, as illustrated in FIG. 4D–4F. At that point, the next clip 28' is ready for application. The purpose of temporarily immobilizing idler rack 84 is to allow the closure member to retreat proximally a sufficient amount to allow the crimping members 58 and 60 to spread sufficiently before the feeder 30 advances the next clip 28' to position between crimping members 58 and 60. Without such a delay, a possibility of jamming could exist if the feeder 30 advances the next clip 28' prior to the crimping members 58 and 60 having had an opportunity to spread far enough to accept the next clip 28'.

Figure 11A:
FIG. 11A illustrates a partial cutaway view of an alternative embodiment of a stapler showing a formed staple.
Figure 11B:
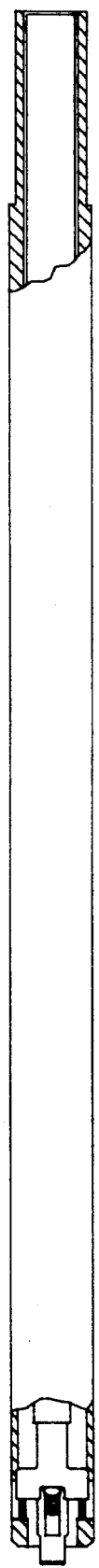
FIG. 11B is the stapler of FIG. 11A in a different position with the staple ejected.
Figure 11C:
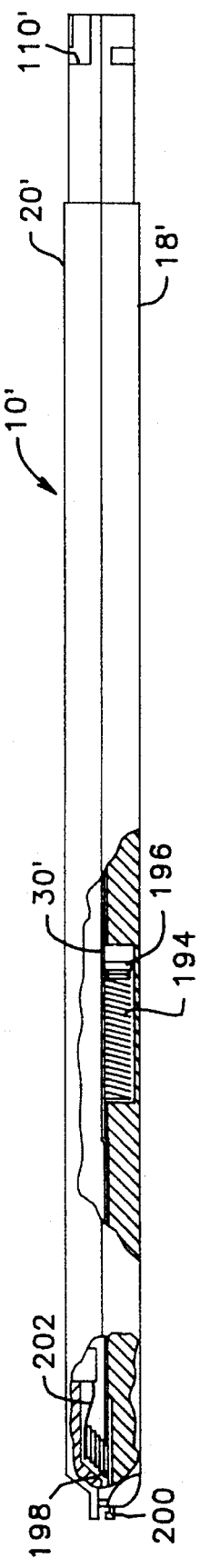
FIG. 11C is an elevational view of the alternative embodiment shown in FIG. 11A in partial cutaway.

FIGS. 11A–11C illustrate a stapler 10' which can be connected to the actuator 14 or the extension member 12 in the manner previously described. In the embodiment illustrated in FIGS. 11A–11C, an L-shaped slot 110' is used in the manner previously described. A feeder 30' is mounted for reciprocal movement within a top cartridge housing 20' and a bottom housing 18'. A return spring 194 is mounted to the bottom housing 18' and bears on tab 196 to bias the feeder 30' in the proximal direction. The feeder 30' is actuated in a distal direction by using an actuator 14, which causes rod 136 to contact the feeder 30' in the manner previously described to move the feeder 30' distally advancing a staple 198 toward anvil 200. The staple 198 is formed around anvil 200 due to the advancement of feeder 30'. Upon release of the trigger 118, spring 194 pushes proximally on tab 196 which causes feeder 30' to move proximally. At that point, pusher 202 pushes the next staple in line downwardly into the forming path so that upon subsequent distal movement of feeder 30', the entire process is repeated.

Figure 13A:
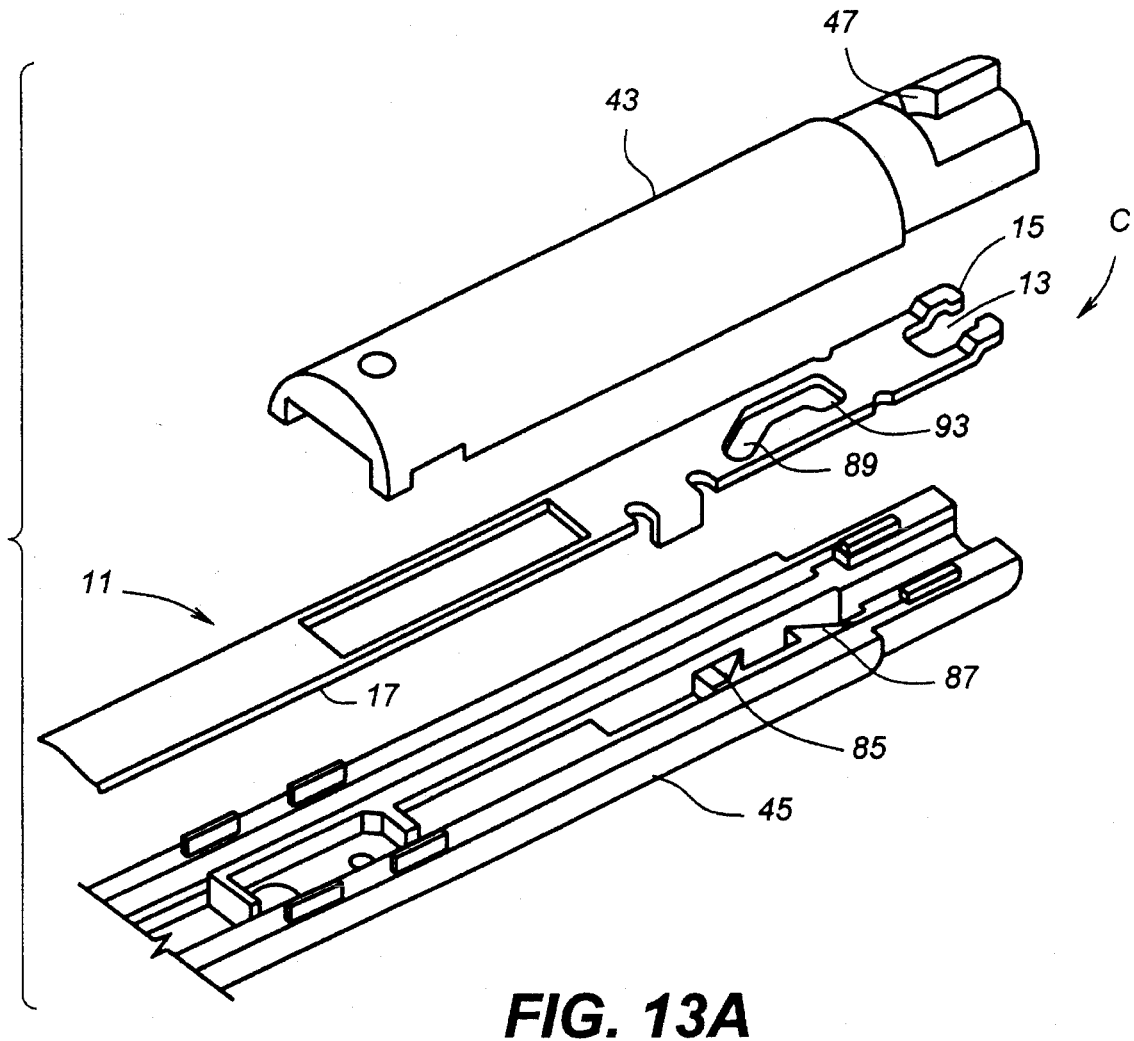
FIG. 13A is an exploded view of the proximal end of the end of the cartridge end assembly.

As previously described, distal movement of the closure member 52 occurs when rod 136 abuts against it and pushes it distally. Return movement of the closure member was accomplished using spring 62. In the embodiment that is shown in the exploded view of FIG. 1, as well as FIG. 9, a relaxation of the handle 14 would not necessarily result in a pull in the proximal direction on the closure member 52. In the alternative embodiment, illustrated in FIGS. 13A and B through 25 alternative configurations of the closure member 52 and rod 136 are disclosed to address the issue of application of a positive force in the proximal direction on the closure member from the drive rod. For simplification, although there is some overlap in parts, new numbers will be applied to the components described in FIGS. 13A–25 for simplicity. As shown in FIG. 13A, the closure member 11 has a different design at its proximal end. A proximally oriented C-shaped opening 13 is illustrated in the FIG. 13A. The proximal end 15 is on a higher plane than the plane of the balance of the closure member 11 which is generally indicated by numeral 17. As a result, there is a bent section giving the proximal end 15 a "dogleg" shape. FIG. 15 illustrates in plan view the C-shaped opening 13. The bent sections 19 form the transition from the plane 17 of the closure member 11 for most of its length and its proximal end 15 which is disposed slightly above. Extending into C-shaped opening 13 are a pair of detents 21 which are in the same plane as each other adjacent proximal end 15.

Figure 12:
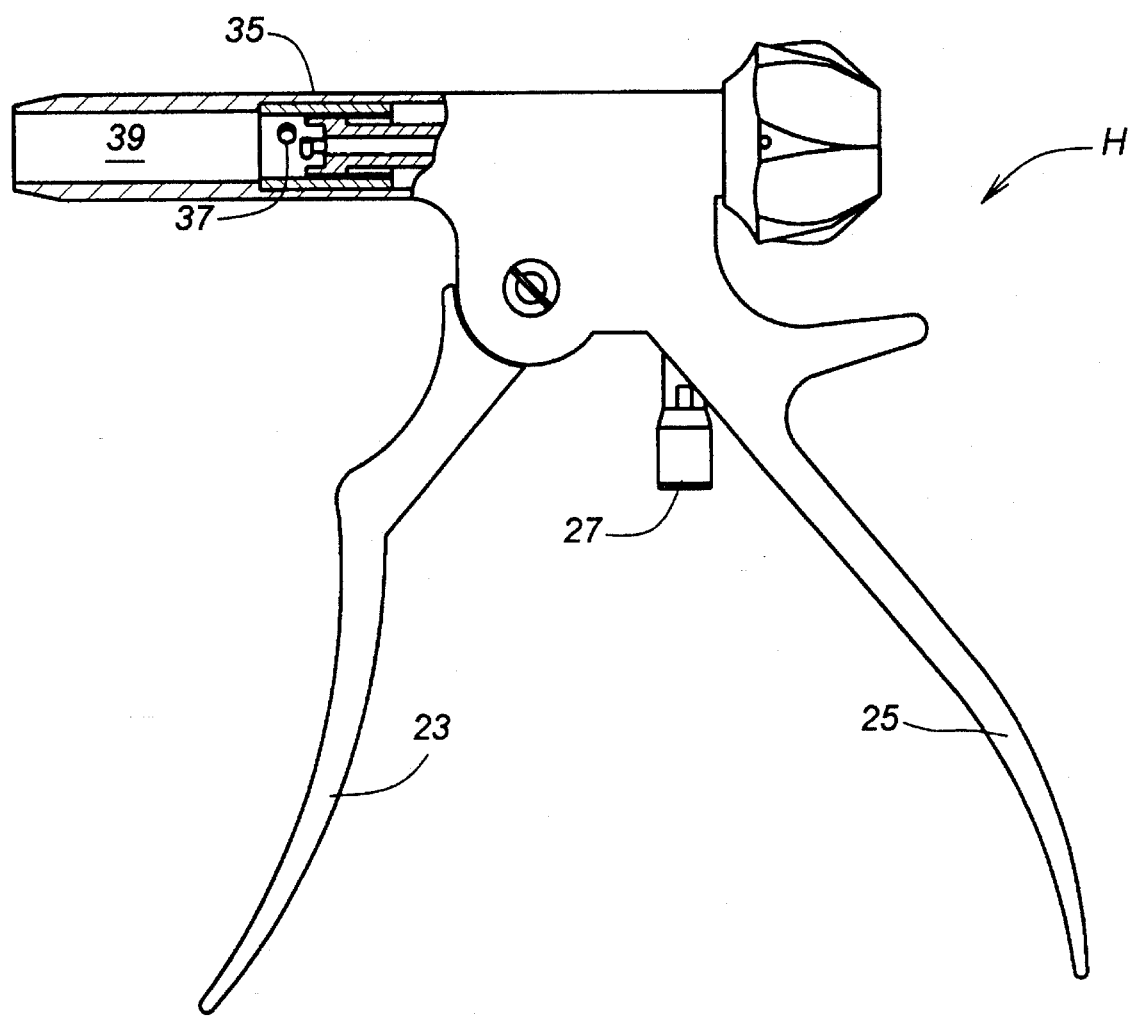
FIG. 12 is an elevational part section view of the handle stem assembly.
Figure 13B:
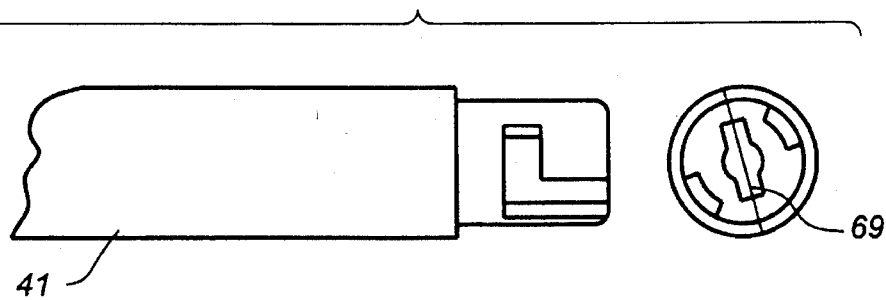
FIG. 13B is an elevational view of the cover assembled over the plug and cartridge bottom members and an end view thereof.

FIG. 12 illustrates the handle stem assembly H, which has a pair of grips 23 and 25. Plunger assembly 27 facilitates disassembly for cleaning. Movement of grip 23 toward grip 25 actuates piston 29 (see FIG. 14) which is operably connected to drive rod 31 for tandem movement as will be described below. A spring 33 biases piston 29 in the proximal direction thus putting an additional force in the proximal direction on drive rod 31. Thus, when grip 23 is released, spring 33 can push back piston 29 to accomplish a force in the proximal direction on closure member 11. Also included as part of the handle stem assembly H is coupling 35 which has a pair of bayonet pins 37 extending into bore 39. As shown in FIGS. 13A–13B, a cover tube 41 slips over a plug member 43. Plug member 43 along with cartridge bottom 45, when put together cover the internal components as previously described which include the alternative embodiment of closure member 11, define the cartridge end assembly C illustrated in FIG. 13A. Plug 43 and cartridge bottom 45 have an L-shaped slot 47. The slot is not visible in FIG. 13A on cartridge bottom 45 but is the mirror image of the one shown in the plug member 43.

Referring now to FIG. 14, a locking element 49 is movably mounted within coupling 35. Spring 51 and knob 53 bear down on sleeve 55 which in turn pushes on locking element 49. Locking element 49 has a pair of finger shaped detents 57 whose cross-sectional area may be seen in FIG. 19. Spring 51 biases locking element 49 in the distal direction until the force from spring 51 is overcome during assembly of the cartridge end assembly C to the handle stem assembly H, as illustrated in FIGS. 17–25.

As illustrated in FIG. 13A and 15, end 15 of closure member 11 is bent so that detents 21 are in proximate alignment with the center line of drive rod 31. The distal end of drive rod 31 can be seen in FIGS. 16A–16B. FIG. 16A shows the distal end which includes a shaft 59 having a groove 61 behind a head 63. Head 63, as seen on end in FIG. 16B, has a pair of opposed flats 65 which equal the dimension of the grooved component 61 of the drive rod 31. As seen on end, apart from the opposed flats, there are two rounded sections 67 that extend outwardly further than the two flat sections 65.

Referring now to FIG. 13B, when the plug member 43 is assembled to cartridge bottom 45 and seen on end, an opening 69 is presented that is rectangular with a protrusion approximately midpoint resembling the end view shown in FIG. 16B. This view is seen in better detail in FIG. 19. Upon assembly, the flats 65 are arranged in an orientation transverse to the longitudinal length of opening 69. The protrusion in the middle of opening 69 accommodates the end of drive rod 31 when oriented transversely to opening 69. Also visible in FIG. 19 through opening 69 is end 15 of closure member 11. As stated previously, closure member 11 has a C-shaped opening 13 which results in a pair of opposed elongated fingers which hold detents 21.

Figure 17:
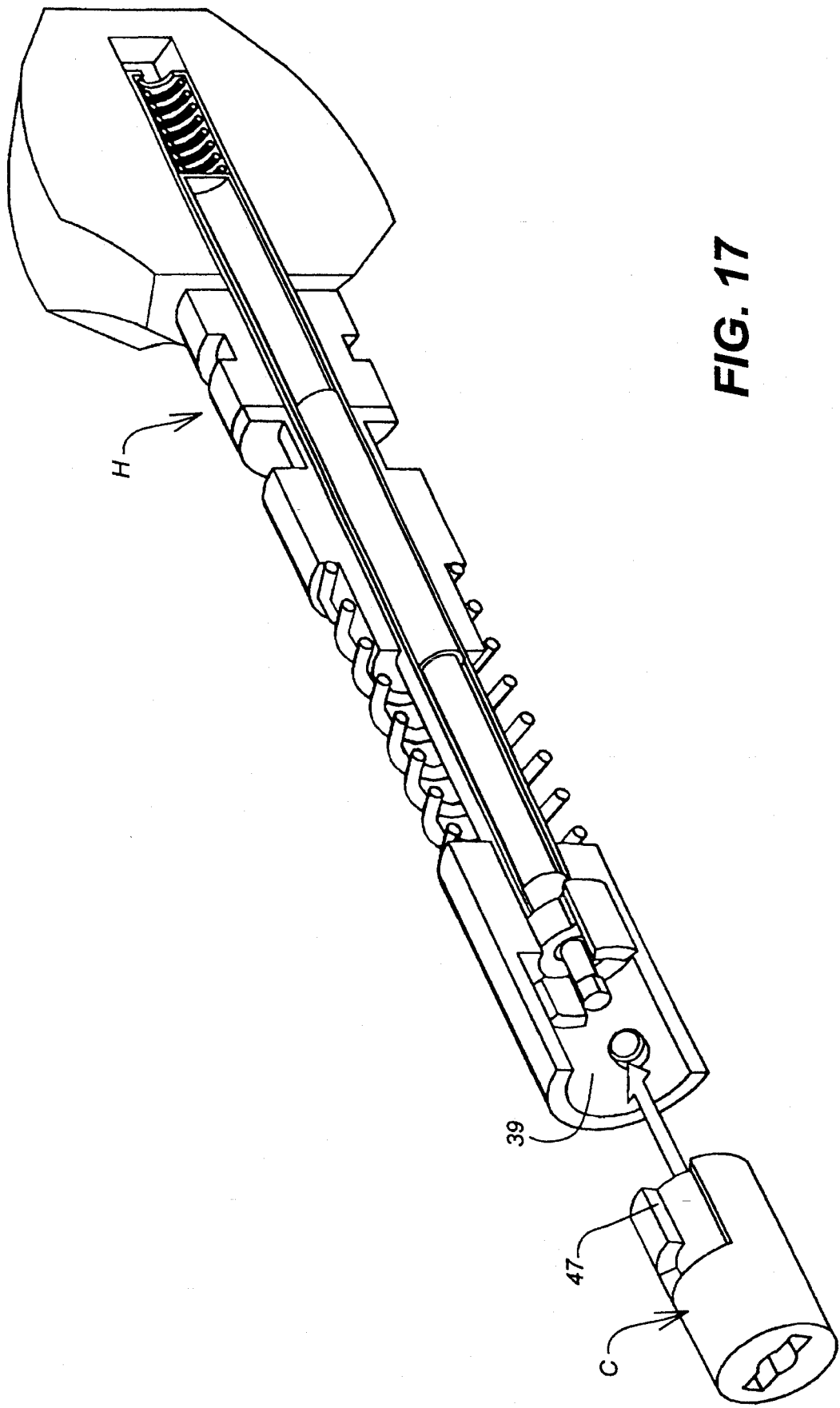
FIG. 17 is a sectional elevational view of the handle stem assembly and cartridge end assembly prior to putting those two components together.
Figure 18:
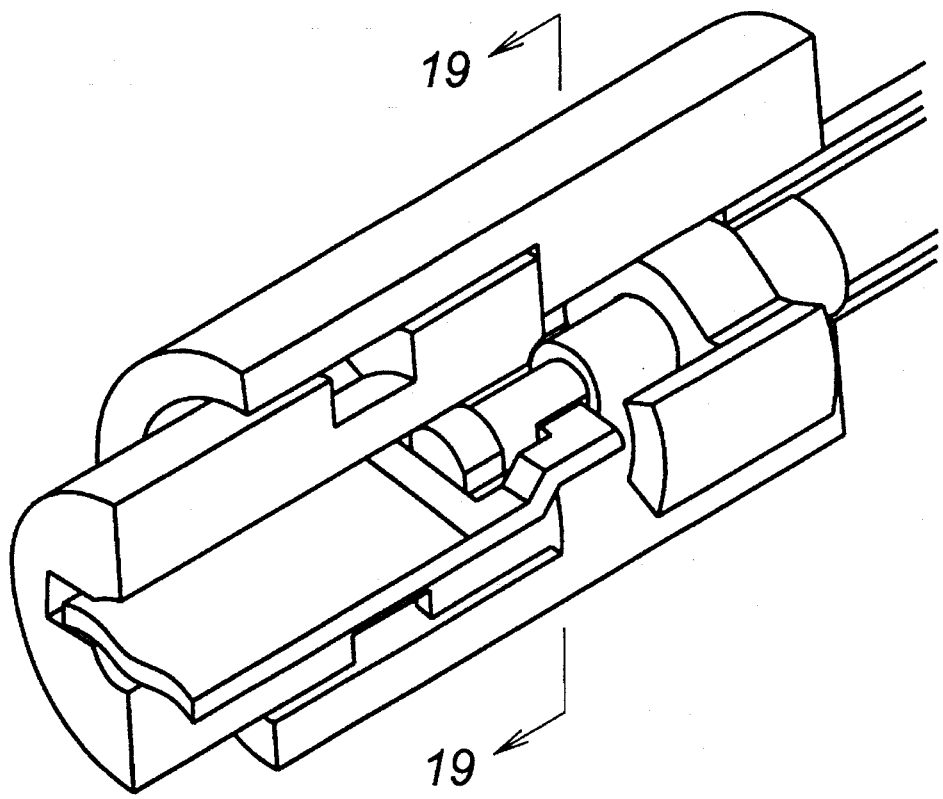
FIG. 18 is the sectional perspective view of FIG. 17 with the two components pushed together.

In assembling the cartridge end assembly C to the handle stem assembly H, the initial position of those two components is illustrated in FIG. 17. In FIG. 17, the initial alignment is made so that the cover tube 41 is aligned with bore 39 so that the L-shaped slot 47 has its longitudinal component in line with bayonet pins 37. FIG. 18 then shows an advancement of the cartridge end assembly C toward to the handle stem assembly H. Various covering components of the handle stem assembly H are removed for clarity of illustration. When the cartridge end assembly C is advanced into bore 39, it displaces in a proximal direction the detents 57 on locking element 49. This occurs because the detents 57 are at this point misaligned with the longitudinal component of L-shaped groove 47. While the motion just described in FIG. 18 is occurring, the head 63 of drive rod 31 is automatically in alignment, shown in FIG. 19, so that the head 63 can advance through the protruding portion of elongated slot 69 to put head 63 into C-shaped opening 13 of closure member 11.

Figure 20:
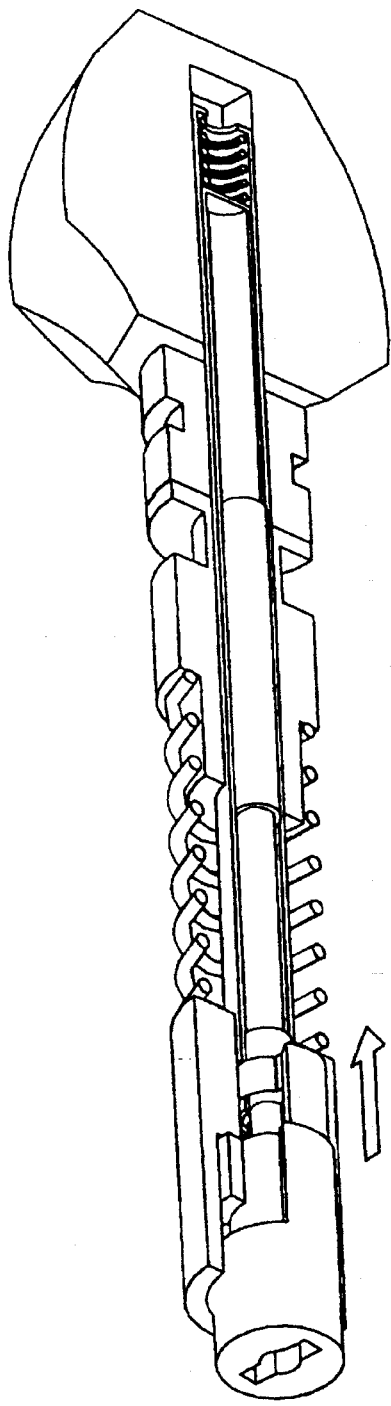
FIG. 20 is the sectional perspective view of FIG. 19 with the locking element displaced rearwardly in the coupling.
Figure 21:
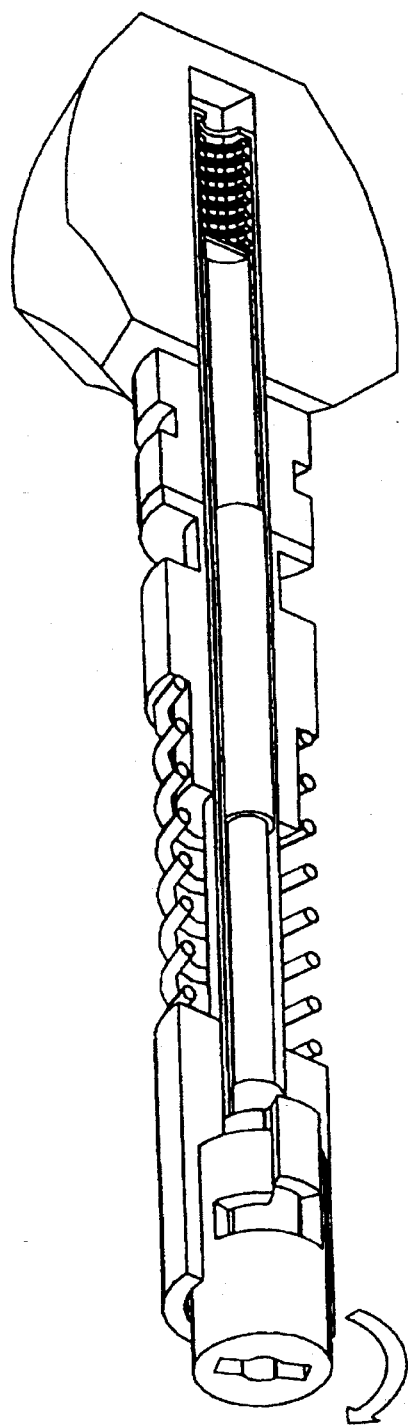
FIG. 21 is the sectional perspective view of FIG. 20 with rotation of the closure member showing alignment of the fingers on the locking member about to occur with the longitudinal slots on the plug.
Figure 22:
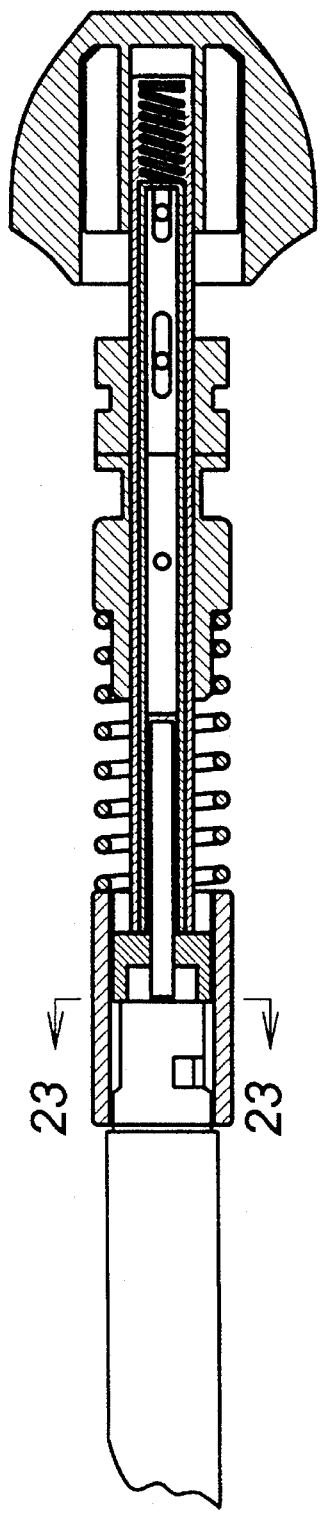
FIG. 22 shows the view of FIG. 21 with further rotation of the cartridge to allow the fingers of the locking element to project into the slots of the plug.
Figure 23:
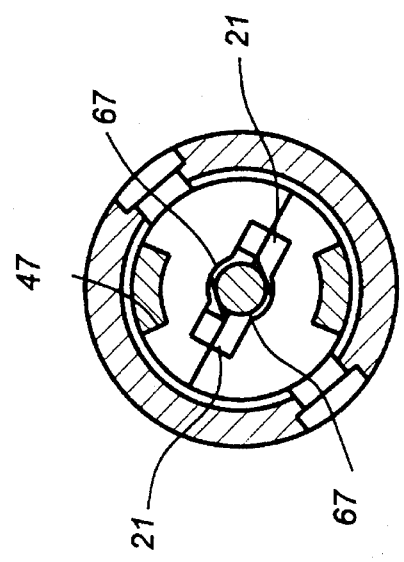
FIG. 23 is a sectional elevational view along lines 23—23 of FIG. 22.

At this point, as shown in FIG. 20, the cartridge end assembly C is pushed into bore 39 until it bottoms out. At that time, it is given a twist as shown in FIG. 21 putting the longitudinal component of L-shaped slot 47 in alignment with detents 57. At that point, spring 51 pushes the detents 57 forward into L-shaped slot 47 thus locking the connection between the cartridge end assembly C and the handle stem assembly H. At this time, the bayonet pins 37 are disposed in the transverse portion of the L-shaped slot 47 found in cartridge end assembly C. Meanwhile, the rotational movement of the cartridge end assembly C with respect to handle stem assembly H described in FIGS. 21 and 22 results in a reorientation of head 63 with respect to opening 69, as shown in FIG. 23. The rounded segments 67 are now literally behind the detents 21 of closure member 11. Accordingly, during operation of the apparatus A when handle grip 23 is released, spring 33 pushes back on piston 29 which is connected to drive rod 31. When this occurs, drive rod 31 moves proximally. Since the rounded segments 67 on drive rod 31 are now trapped in C-shaped opening 13 due to the contact with detents 21, a force in the proximal direction is exerted on closure member 11.

Figure 24:
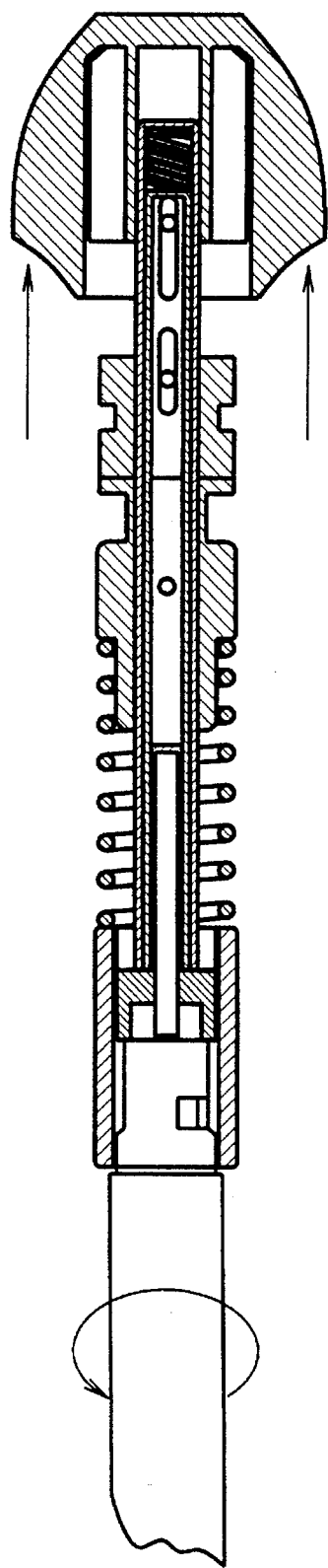
FIG. 24 is the view of FIG. 23 showing the initial step toward disengagement.
Figure 25:
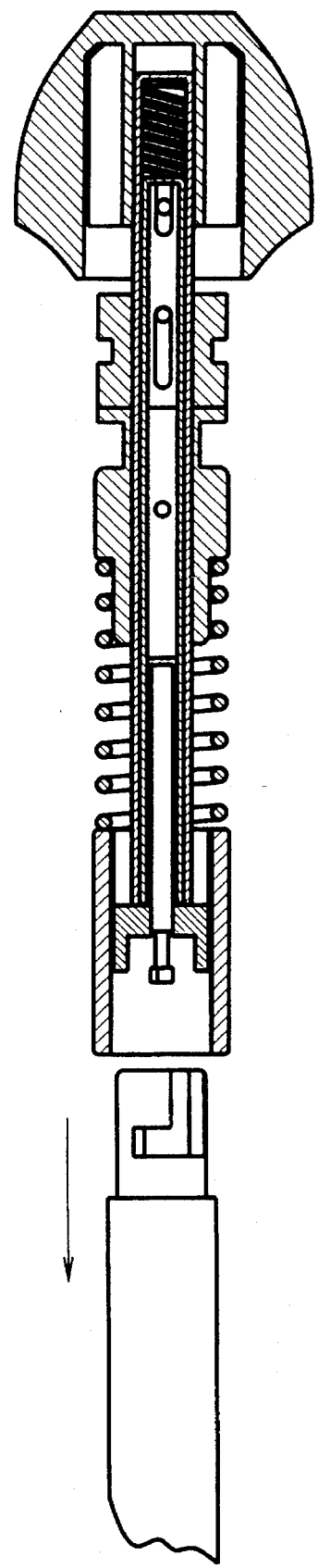
FIG. 25 shows complete disengagement between the cartridge end assembly and the handle stem assembly.

The extension of detents 57 into the longitudinal portion of L-shaped groove 47 also precludes the accidental disconnection between cartridge end assembly C and handle stem assembly H. This connection can be defeated as shown in FIGS. 24 and 25 when it is desired to disconnect the cartridge end assembly C from the handle stem assembly H. In order to do this, knob 53 is pulled back as shown in FIG.

24. When this occurs, detents 57 move in tandem with knob 53 and out of the longitudinal segment of L-shaped groove 47 in the cartridge end assembly C. Having pulled the detents 57 all of the way out of groove 47 as shown in FIG. 24, the cartridge end assembly C can then be rotated to align pins 37 with the longitudinal segment of L-shaped slot 47 so that a pullback as shown in FIG. 25 can be accomplished to separate the cartridge end assembly C from the handle stem assembly H. The handle stem assembly H can then be properly cleaned and reused while the cartridge end assembly C is preferably a disposable product. This generates significant cost savings for the surgeon or hospital using the apparatus A since the entire handle assembly is saved and reused many times over while the more economical components are made to be disposable in the form of a removable cartridge end assembly C.

The dogleg feature described on the proximal end of the closure member 11 allows the drive rod in normal operation to bear down significantly on the closure member to push it distally for closing of the jaw 46. On the other hand, if for any reason the closure member does not easily return thereby allowing the jaw 46 to open, then the apparatus of the present invention allows a positive retraction force in the proximal direction to be applied to closure member 11 from drive rod 31. In order to apply a further force to release the jaw 46, handles 25 a 23 can bend physically separated which will provide a mechanical assist to proximal movement of closure member 11.

Figure 19:
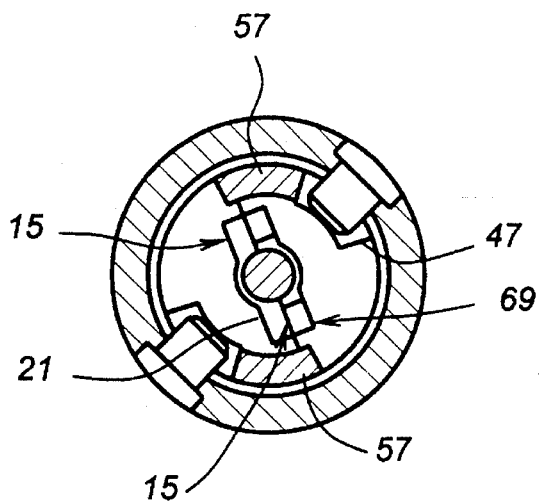
FIG. 19 is a section view along lines 19—19 of FIG. 18.

The positive locking feature which can be seen by comparing FIGS. 19 and 23 allows the surgeon assurance that the accidental separation between the cartridge end assembly C and the handle stem assembly H will not occur. When the detents 57 come into alignment with the groove 47 and are held in place by spring force applied from spring 51, the connection of the two components is assured.

This embodiment illustrated in FIG. 14 also has a detent 71 which includes groove 73. Upon rotation of knob 53, an indexing mechanism not shown gives an audible click upon change of rotational position of detent 71 so that the jaw 46 at the distal end of the apparatus A can have its orientation changed during a procedure in the manner described in FIGS. 9 and 10 of the embodiment.

Figure 26:
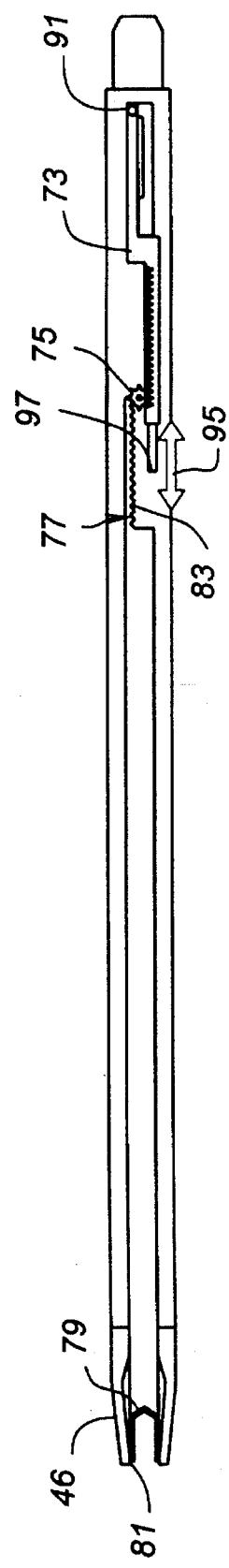
FIG. 26 is a plan view and section of the cartridge end assembly illustrating the last clip lockout feature shown with the last clip between the jaws.
Figure 27:
FIG. 27 is the view of FIG. 26 with no more clips remaining in the cartridge end assembly and the feeder extended between the jaws.
Figure 28:
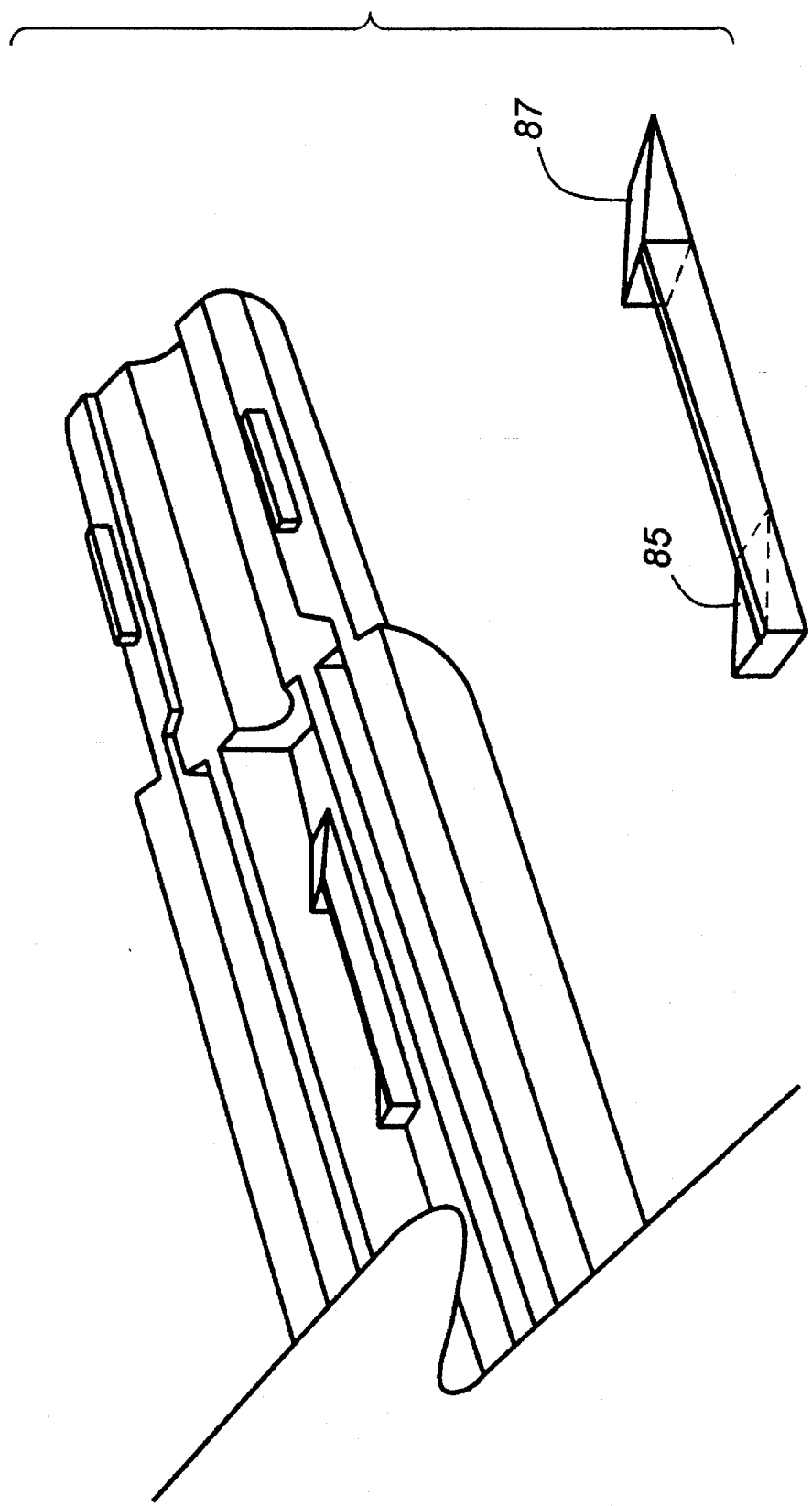
FIG. 28 is a detailed view of the latched teeth built into the cartridge bottom to cartridge end assembly which selectively engage the rack to force the apparatus to completely cycle and to allow a sufficient delay so the jaws could open before the feeder can advance another clip.

Referring now to FIGS. 26-28, the last clip lockout feature will now be described. As previously stated, advancement of the drive rod 31 pushes the closure member 11 forward over the jaws 46 to form the clip 79. When a clip 79 is formed and the grip 23 is released, spring 33, as well as springs 201 (see FIG. 9) act on closure member 11 to move it in the proximal direction. After a predetermined amount of movement, closure member 11 and rack 73 (see FIG. 26) move in tandem. When the rack 73 moves in a proximal direction, it turns gear 75 which in turn drives a feeder 77 in the direction to advance the next clip 79. The jaws 46 have a retainer 81 to catch the next clip 79 which is fed. When the next clip 79 strikes the retainer 81, the forward movement of the feeder is impeded, as shown in FIG. 26. This occurs before the rack on the end of the feeder 77 runs off gear 75.

When the cartridge end assembly C runs out of clips, an undesirable situation can occur which has been prevented by the apparatus A of the present invention. If there are no more clips to feed, the surgeon may want to squeeze the handle 23 at a time when no clip 79 is between the jaws 46. This could create undesirable pinching of vessels or other body organs and cause unnecessary trauma to the patient. It is therefore desirable to prevent the jaws 46 from moving together when there is no clip 79 between them. To accomplish this feature, feeder 77 has its gear teeth 83 continuing all the way to its proximal end. The impact of having this type of design is illustrated by comparing FIG. 26 when a clip 79 is actually fed and FIG. 27 where there are no further clips 79 to be fed. In that situation, the movement of the components previously described is the same. However, since the forward motion of the feeder 77 is no longer stopped by a clip 79 abutting retainer 81, the feeder is free to advance until the feeder itself comes in contact with retainer 81. At that point, the feeder 77 is literally between the jaws 46 up against retainer 81. In that condition, any squeezing on handle 23 will not result in bringing jaws 46 together which could cause additional trauma to the patient if any organ or vessel is pinched therebetween.

Referring now to FIGS. 13A and 28, it can be seen that the cartridge bottom 45 has a pair of integrally formed teeth 85 and 87. The closure member 11 has a slot 89. The rack 73 has a transversely-positioned cylinder 91 (see FIG. 26) at its proximal end. Cylinder 91 extends upwardly into slot 89 and downwardly so that it can interact with teeth 85 and 87. As the closure member 11 moves in a distal direction to close the jaws 46, the rack 73 is carried with the closure member 11 due to portions of cylinder 91 extending into slot 89 at its proximal end 93. As the cylinder 91 is advanced distally, it climbs up the ramp of tooth 87 and falls distally behind it. Once this occurs, even if the handle 23 is released, the apparatus A must be fully cycled so that the clip that is at that time in the jaw 46 is fully formed. Thus, even if the surgeon releases the handle 23 he or she must still regrasp the handle 23 and continue squeezing to complete the cycle. Further distal movement of closure member 11 takes with it the cylinder 91 on rack 73 until such time as the rack 73 climbs up the ramp of tooth 85 and falls on the distal side of that tooth. At that point, the feeder 77 has come back sufficiently so that the next clip 79 can fall down in front of it. At that point, if the handle 23 is released the previous clip will fall out and the clip 79 that has just fallen down in front of the feeder will be fed. This occurs when the handle 23 is released allowing the closure member 11 to move in the proximal direction. At this time, a spring illustrated by arrow 95 urges the rack 73 proximally. Initially, the closure member 11 moves proximally a very small distance until cylinder 91 is engaged by the second tooth. At that point, the closure member 11 continues to move proximally as cylinder 91 is then urged to move away from proximal end 93 of slot 89 (see FIG. 13A). Further proximal movement of the closure member 11 ramps the cylinder 91 along the dogleg portion of slot 89 which allows cylinder 91 to clear tooth 85. A spring illustrated by arrow 95 (see FIG. 26) acts on the distal end 97 of rack 73 to begin urging the rack in a proximal direction. The same thing occurs as the closure member 11 continues to move in a proximal direction again ramping cylinder 91 on rack 73 over tooth 87. At that point, spring 95 can continue proximal movement along with the closure member 11. This proximal movement of rack 73 in turn is translated into distal movement of the feeder 77 through gear 75. Another view of the teeth 85 and 87 which are built into cartridge bottom 45 is illustrated in FIG. 28.

In all other ways, the cartridge end assembly C functions in the manner described for the embodiment in FIGS. 1–11.

The foregoing disclosure and description of the invention are illustrative and explanatory thereof, and various changes in the size, shape and materials, as well as in the details of the illustrated construction, may be made without departing from the spirit of the invention.

What is claimed is:

1. A method of performing a surgical procedure, comprising the steps of:
   joining a handle assembly to a cartridge assembly;
   operatively connecting a single operating member in said handle assembly to a closure member or a feeder in said cartridge assembly;
   operatively connecting said closure member to a clip feeder in said cartridge assembly such that movement of said closure member in one direction results in movement of said feeder in an opposite direction;
   selectively driving one of said closure member or feeder in a proximal or distal direction substantially in tandem with said single operating member which in turn actuates reverse movement of the other;
   forming a clip with distal movement of said closure member; and
   feeding a new clip with proximal movement of said closure member.

2. A method of forming clips comprising:
   feeding a clip into a jaw with a feeder;
   forming a clip by closing a jaw with a closure member;
   driving said feeder in an opposite direction from said closure member;
   using a rotatable member for creation of said opposed movement;
   retracting said closure member allowing said jaw to open;
   driving said feeder into said jaw when no more clips remain to be fed; and
   releasing said feeder from said rotating member during said driving step.

3. The method of claim 2 further comprising:
   allowing the closure member to move proximally for a fixed distance prior to engaging said feeder; and
   engaging said rotatable member for opposed motion of said feeder only after sufficient proximal movement of said closure member to open said jaw.

4. A clip forming apparatus comprising:
   a cartridge assembly further comprising:
     a housing;
     means in said housing for storing clips, further comprising a feeder;
     means in said housing for forming clips;
     said means for forming further comprising:
     a closure member;
     a jaw operably connected to said closure member;
     means for mounting said closure member to said feeder within said cartridge assembly such that movement of said closure member in one direction results in movement of said feeder in an opposite direction;
   a handle assembly further comprising:
     a single movably mounted operating member;
     actuating means for selective movement of said operating member;
     said handle assembly releasably mounted to said cartridge assembly; and
     said single operating member operatively engaged to one of said closure member or said feeder when said handle assembly is selectively connected to said cartridge assembly for urging one of said closure member or said feeder selectively in two opposed directions to feed and form a clip.

5. The apparatus of claim 4 wherein:
   said closure member has a proximal end formed having an opening, said opening proximally oriented;
   at least one detent on said closure member oriented into said opening; and
   said operating member when assembled into said cartridge assembly operably engageable to said detent for applying a force thereto.

6. The apparatus of claim 1 wherein: said operating member is operably engageable with said detent to apply a force in proximal direction to said closure member to urge it away from said jaw thereby facilitating opening of said jaw; and
   said operating member also abuts said closure member in said opening to urge it distally for closing said jaw.

7. The apparatus of claim 6 wherein:
   said cartridge assembly housing defines an opening formed at its proximal end to accept said operating member into said opening in said closure member;
   alignment means on said cartridge and handle assembly to facilitate a first orientation therebetween as said cartridge and handle assemblies are selectively joined together; and
   said operating member aligned with said openings in said housing and said closure member as a result of said alignment created by said alignment means.

8. The apparatus of claim 7 further comprising:
   securing means on said handle assembly to secure attachment between said handle and cartridge assembly, said securing means operable with said alignment menas for selectively securing said handle and cartridge assembly in a second orientation.

9. The apparatus of claim 1 wherein:
   said feeder is operably engaged to said closure member for selective opposed movement with respect to said closure member during at least a portion of the time when said operating member causes movement of said closure member.

10. An apparatus for forming clips comprising:
    a housing;
    an actuator connected to said housing;
    at least one clip stored in said housing;
    a feeder in said housing for feeding said clip;
    a reciprocating closure member in said housing;
    said feeder operably connected to said closure member in said housing for selective opposed operation responsive to application of a force to said feeder or said closure member by said actuator;
    a jaw movable responsive to said closure member for forming a clip after said feeder has fed the clip and been retracted from within said jaw; and
    said feeder movable into said jaw to prevent operation thereof after the last clip in said housing has been formed by said jaw.

11. The apparatus of claim 10 wherein:
    said feeder and said closure member are operatively engaged for opposed movement; and
    said operative engagement being defeated upon movement of said feeder into said jaw.

12. A clip forming apparatus comprising:
    a cartridge assembly further comprising:
      a housing;
      means in said housing for storing clips;
      means in said housing for forming clips;
      said means for forming further comprising:
      a closure member;
      a jaw;

said closure member movably mounted to said jaw; and a handle assembly further comprising:
a movably mounted operating member;
actuating means for selective movement of said operating member;
said handle assembly releasably mounted to said cartridge assembly;
said operating member operatively engaged to said closure member when said handle assembly is selectively connected to said cartridge assembly for urging said closure member selectively in two directions for opening and closing said jaw;

said closure member has a proximal end formed having an opening, said opening proximally oriented;

at least one detent on said closure member oriented into said opening;

said operating member when assembled into said cartridge assembly operably engageable to said detent for applying a force thereto;

said operating member is operably engageable with said detent to apply a force in proximal direction to said closure member to urge it away from said jaw thereby facilitating opening of said jaw;

said operating member also abuts said closure member in said opening to urge it distally for closing said jaw;

said cartridge assembly housing refines an opening formed at its proximal end to accept said operating member into said opening in said closure member; p1 alignment means on said cartridge and handle assembly to facilitate a first orientation therebetween as said cartridge and handle assemblies are selectively joined together;

said operating member aligned with said openings in said housing and said closure member as a result of said alignment created by said alignment means;

securing means on said handle assembly to secure attachment between said handle and cartridge assembly, said securing means operable with said alignment means for selectively securing said handle and cartridge means in a second orientation;

rotation of said cartridge assembly while engaged to said alignment means orients said cartridge and handle assemblies in said second orientation;

said operating member formed to clear past said detent in a first position to enter said opening in said closure member; and said rotation reorienting said operating member from a first position where it clears past said detent to enter said opening in said closure member, to a second position where said operating member is at least in part positioned transverse to said detent to allow application of force in a proximal direction for opening said jaw by contact of said operating member with said detent.

13. The apparatus of claim 12 wherein:

said alignment means further comprises;

at least one slot on said cartridge said slot having a substantially longitudinal component and a substantially transverse component;

at least one pin in said handle assembly; and said securing means further comprises a locking member on said handle assembly initially misaligned with said longitudinal component of said slot in said first orientation and aligned with said longitudinal component of said slot in said second orientation.

14. The apparatus of claim 13 wherein:

said pin is disposed in said transverse component of said slot in said second orientation; and biasing means in said handle assembly allowing said locking member to be selectively displaced proximally in said first orientation and to bias said locking member distally in said second orientation into said longitudinal component of said slot.

15. The apparatus of claim 4 wherein:

said biasing means comprises a spring;

said handle assembly further comprises a retractable knob, said knob when selectively retracted overcomes a force on said locking member from said spring while pulling said locking member out of said longitudinal component of said slot.

16. The apparatus of claim 15 wherein:

said opening in said closure member is formed by a pair of opposed fingers with said detent mounted on at least one of said fingers; and said knob rotatably mounted in said handle assembly such that rotation of said knob causes said operating member to apply a rotational force to said closure member to reorient said jaw during a surgical procedure.

17. The apparatus of claim 12 wherein:

said operating member further comprises a head;

said head formed having a generally cylindrical section with a pair of opposed flats and a pair of opposed rounded sections;

said opening in said housing having a portion thereof conforming to the shape of said head and oriented to accept said head in said first orientation of said handle and cartridge assemblies; and said rounded sections are put in misalignment with said detent on said closure member in said second orientation of said handle and said cartridge assembly.

18. A clip forming apparatus comprising:

a cartridge assembly further comprising:
a housing;
means in said housing for storing clips;
means in said housing for forming clips;
said means for forming further comprising:
a closure member;
a jaw;
said closure member movably mounted to said jaw;

a handle assembly further comprising:
a movably mounted operating member;
actuating means for selective movement of said operating member;
said handle assembly releasably mounted to said cartridge assembly;
said operating member operatively engaged to said closure member when said handle assembly is selectively connected to said cartridge assembly for urging said closure member selectively in two directions for opening and closing said jaw;

said means for forming further comprises a feeder mounted for selective reciprocal operation;

said feeder operably engaged to said closure member for selective opposed movement with respect to said closure member during at least a portion of the time when said operating member causes movement of said closure member;

said cartridge assembly further comprises:
a rotatably mounted member connected between said feeder and said closure member further comprising at least one rounded element to effect a reversal of motion therebetween.

19. The apparatus claim 18 wherein:

said rotatably mounted member further comprises at least two gears, said closure member and said feeder, each having a rack meshing with one of said gears; and said feeder and said closure member are stacked within said housing while engaged to said gears.

20. The apparatus of claim 1 wherein:

said gears have a different number of teeth such that movement of said closure member results in a different amount of opposed movement of said feeder.

21. The apparatus of claim 10 wherein:

said rack for said closure member is formed as a separate component, said closure member movable at least in part during its travel independently of said rack for said closure member;

said closure member rack further comprising a latch to selectively hold said rack stationary with respect to said housing as said closure member is moved in a proximal direction to open said jaw; and a release mechanism on said closure member to defeat said latch after a predetermined movement in the proximal direction by said closure member whereupon said closure member rack is freed to move proximally and in turn advance said feeder distally through interaction of said gears.

22. The apparatus of claim 21 wherein:

said housing contains a plurality of clips in line;

said latch holding said gears and feeder stationary until said release mechanism which comprises a cutout on said closure defeats said latch mechanism by a camming action upon a predetermined movement of said closure member to a point where said jaw opens sufficiently to accept another clip; and biasing means acting on said closure member rack operable to accelerate said closure member rack upon said camming, whereupon movement initiated by said biasing means spins said gears allowing said feeder to advance the next one of said clips only after said jaw has opened is sufficiently to accept it.

23. The apparatus of claim 19 wherein:

said rack on said feeder extends to its proximal end;

whereupon in the absence of a clip ahead of said feeder proximal movement of said operating member allows said gear in contact with said rack on said feeder to propel said feeder distally into said jaw; and said rack on said feeder moving away from contact with said gear upon having its distal motion stopped by said jaw.

24. A method of performing a surgical procedure comprising the steps of:

joining a handle assembly to a cartridge assembly;

operatively connecting a operating member in said handle assembly to a closure member in said cartridge assembly;

operatively connecting said closure member to a clip feeder for reverse movements therebetween;

selectively driving said closure member in a proximal or distal direction substantially in tandem with said operating member;

forming a clip with distal movement of said closure member;

feeding a new clip with proximal movement of said closure member;

said operably connecting step for said operating member is accomplished in said joining step;

said operably connecting said closure member to said feeder further comprising;
  providing gearing between said closure member and said feeder; and
  disposing said closure member and said feeder on opposed sides of said gearing.

25. The method of claim 24 further comprising the steps of:

facilitating alignment between said handle and cartridge assemblies with a pin/slot combination;

advancing said slot in said cartridge assembly over said pin in said handle assembly;

displacing a detent in said handle assembly by said advancing;

aligning said operating member within an opening on said closure member by said advancing;

rotating said cartridge assembly with respect to said handle assembly;

trapping said operating member to said opening in said closure member by said rotating; and allowing said detent to be biased into said slot by said rotating.

26. A clip forming apparatus comprising:

a cartridge assembly further comprising:
  a housing;
  means in said housing for storing clips;
  means in said housing for forming clips;
  said means for forming further comprising:
    a closure member;
    a jaw;
    said closure member movably mounted to said jaw; and a handle assembly further comprising:
  a movably mounted operating member;
  actuating means for selective movement of said operating member;
  said handle assembly releasably mounted to said cartridge assembly;
  said operating member operatively engaged to said closure member when said handle assembly is selectively connected to said cartridge assembly for urging said closure member selectively in two directions for opening and closing said jaw;

said means for forming further comprises a feeder mounted for selective reciprocal operation;

said feeder operably engaged to said closure member for selective opposed movement with respect to said closure member during at least a portion of the time when said operating member causes movement of said closure member; and said feeder is selectively disengageable from said engagement to said closure member for movement into said jaw when said means for storing clips becomes empty.

27. An apparatus for forming clips comprising:

a housing;

at least one clip stored in said housing;

a reciprocating closure member in said housing;

a jaw movable responsive to said closure member for forming a clip;

said feeder movable into said jaw to prevent closure thereof after the last clip in said housing has been formed by said jaw;

said feeder and said closure member are operatively engaged for opposed movement;

said operative engagement being defeated upon movement of said feeder into said jaw;

said feeder and said closure member are operatively engaged for opposed movement;

said operative engagement being defeated upon movement of said feeder into said jaw;

said housing comprises a rotatably mounted member connected on opposed sides to said feeder and said closure member; and whereupon discharge of the last of said at least one clip, proximal movement of said closure member creates opposed distal movement of said feeder and propels said feeder away from said rotatably mounted member, disabling said feeder from further movement by said rotatably mounted member.

28. The apparatus of claim 35 wherein:

said feeder is formed having a rack on the proximal end thereof;

said rotatably mounted member comprises at least one gear selectively engageable to said rack on said feeder;

said jaw stopping a clip ahead of said feeder while its rack is still engaged to said gear; and said feeder advancing into said jaw when no clip is disposed in front of it as a result of a distal force from said gear of said rack of said feeder resulting in said rack becoming disconnected from said gear.

29. The apparatus of claim 28 wherein:

said rack on said feeder extends to the proximal end of said feeder;

said rotatably mounted member has a plurality of gears for engagement of said closure member and said feeder; and lost motion means on said closure member to allow said closure member to move proximally a sufficient amount to open said jaw before activation of said gears drives said feeder distally either with the next clip to be fed or into said jaw when no clip remains in said housing.

* * * * *